United States Patent
Nishimura et al.

(10) Patent No.: US 8,598,125 B2
(45) Date of Patent: Dec. 3, 2013

(54) CDCA1 PEPTIDE AND PHARMACEUTICAL AGENT COMPRISING THE SAME

(75) Inventors: Yasuharu Nishimura, Kumamoto (JP); Michiko Harao, Kumamoto (JP); Takuya Tsunoda, Kanagawa (JP); Yusuke Nakamura, Tokyo (JP)

(73) Assignee: Onco Therapy Science, Inc., Kanagawa (JP)

( * ) Notice: Subject to any disclaimer, the term of this patent is extended or adjusted under 35 U.S.C. 154(b) by 344 days.

(21) Appl. No.: 12/673,434

(22) PCT Filed: Jun. 13, 2008

(86) PCT No.: PCT/JP2008/060837
§ 371 (c)(1),
(2), (4) Date: Feb. 25, 2011

(87) PCT Pub. No.: WO2009/025117
PCT Pub. Date: Feb. 26, 2009

(65) Prior Publication Data
US 2011/0152199 A1    Jun. 23, 2011

(30) Foreign Application Priority Data
Aug. 20, 2007   (JP) .................. 2007-214000

(51) Int. Cl.
*A61K 38/00* (2006.01)
(52) U.S. Cl.
USPC ........... 514/19.2; 530/326; 530/327; 530/328
(58) Field of Classification Search
None
See application file for complete search history.

(56) References Cited

U.S. PATENT DOCUMENTS

| | | | |
|---|---|---|---|
| 6,699,703 B1 * | 3/2004 | Doucette-Stamm et al. ................. | 435/252.3 |
| 6,858,204 B2 * | 2/2005 | Henderson et al. ........ | 424/93.1 |
| 6,867,283 B2 | 3/2005 | Barnea et al. | |
| 7,214,786 B2 * | 5/2007 | Kovalic et al. .............. | 536/23.6 |
| 7,531,300 B2 | 5/2009 | Nakamura et al. | |
| 7,776,341 B2 * | 8/2010 | Belisle et al. .............. | 424/248.1 |
| 2002/0172952 A1 | 11/2002 | Henderson et al. | |
| 2006/0024692 A1 | 2/2006 | Nakamura et al. | |
| 2006/0088527 A1 | 4/2006 | Henderson et al. | |
| 2006/0216301 A1 | 9/2006 | Tahara et al. | |
| 2009/0175844 A1 | 7/2009 | Nakamura et al. | |
| 2009/0208514 A1 | 8/2009 | Nakamura et al. | |
| 2009/0215683 A1 | 8/2009 | Nakamura et al. | |
| 2009/0286856 A1 | 11/2009 | Nakamura et al. | |
| 2009/0317392 A1 | 12/2009 | Nakamura et al. | |
| 2012/0014996 A1 | 1/2012 | Nakamura et al. | |

FOREIGN PATENT DOCUMENTS

| | | |
|---|---|---|
| EP | 2186889 A1 | 5/2010 |
| JP | 2004-500029 A | 1/2004 |
| JP | 2004-512824 A | 4/2004 |
| JP | 2006-500949 A | 1/2006 |
| WO | WO 98/53071 A1 | 11/1998 |
| WO | 01/00828 A2 | 1/2001 |
| WO | 01/22920 A2 | 4/2001 |
| WO | 02/04514 A2 | 1/2002 |
| WO | WO 02/094981 A2 | 11/2002 |
| WO | 03/025010 * | 3/2003 |
| WO | 03/105891 A2 | 12/2003 |
| WO | WO 2004/024766 A1 | 3/2004 |
| WO | WO 2004/031410 A2 | 4/2004 |
| WO | WO 2004/031413 A2 | 4/2004 |
| WO | WO 2004/055050 A2 | 7/2004 |
| WO | 2004/080148 A2 | 9/2004 |
| WO | WO 2005/028676 A2 | 3/2005 |
| WO | WO 2005/089735 A2 | 9/2005 |
| WO | WO 2006/085684 A2 | 8/2006 |
| WO | WO 2007/013480 A2 | 2/2007 |
| WO | WO 2007/013665 A2 | 2/2007 |
| WO | WO 2007/013671 A2 | 2/2007 |
| WO | WO 2009/153992 A1 | 12/2009 |
| WO | 2011/030329 A1 | 3/2011 |

OTHER PUBLICATIONS

Wigge et al J. Cell Biol. vol. 152 p. 349 (2001).*
Freshney (Culture of Animal Cells, A Manual of Basic Technique, Alan R. Liss, Inc., 1983, New York, p. 4).*
Dermer (Bio/Technology, 1994, 12:320).*
Gura (Science, 1997, 278:1041-1042).*
Jain (Sci. Am., 1994, 271:58-65).*
Ezzell (J. NIH Res. 1995 7:46).*
Spitler (Cancer Biotherapy, 1995, 10:1-3).*
Johnson et al, Cancer Treatment Reviews vol. 2p. 1, (1975).*
Engelhard, Current Opinion in Immunology vol. 6 p. 13 (1994).*
Guo, et al Nature vol. 360 p. 384 (1992).*
Rammensee et al, Immunogenetics vol. 41 p. 178 (1995).*
Shastri et al J. Immunol. vol. 1995 vol. 155 p. 4339.*
U.S. Appl. No. 12/999,051, filed Apr. 22, 2011, 41 pages.
DeLuca, J., et al., "Nuf2 and Hec1 Are Required for Retention of the Checkpoint Proteins Mad1 and Mad2 to Kinetochores," *Current Biology*, vol. 13(23), pp. 2103-2109 (Dec. 2, 2003).
DeLuca, J., et al., "Hec1 and Nuf2 Are Core Components of the Kinetochore Outer Plate Essential for Organizing Microtubule Attachment Sites," *Molecular Biology of the Cell*, vol. 16(2), pp. 519-531 (Feb. 2005).
DeLuca, J., et al., "hNuf2 inhibition blocks stable kinetochore-microtubule attachment and induces mitotic cell death in HeLa Cells," *The Journal of Cell Biology*, vol. 159(4), pp. 549-555 (Nov. 25, 2002, Epub Nov. 18, 2002).
Harao, M., et al., "CDCA1, a novel cancer-testis antigen useful for immunotherapy of lung cancer," *Nihon Gangakkaisokai, Proceedings 66th Annual Meeting of the Japanese Cancer Association*, p. 163-4, Abstract #P-294 (2007).
Harao, M., Doctor's Thesis, pp. 1-49 (2008).

(Continued)

*Primary Examiner* — Sheela J Huff
(74) *Attorney, Agent, or Firm* — Kilpatrick Townsend & Stockton LLP

(57) ABSTRACT

The present invention provides the peptide of (A) or (B) below, and methods of using the peptide:
(A) a peptide including the amino acid sequence of SEQ ID NO: 1 or 2,
(B) a peptide which includes the amino acid sequence of SEQ ID NO: 1 or 2, wherein one, two, or several amino acid(s) are substituted, deleted, inserted, and/or added, and wherein the peptide shows killer T cell-inducing activity.

11 Claims, 4 Drawing Sheets

(56) References Cited

OTHER PUBLICATIONS

Harao, "Identification of a novel cancer-testis antigen, CDCA1, that is useful for immunotherapy for lung cancer," *Nihon Gekagakkai*, 108, p. 282, Abstract #SF-077-1 (2008).

Harao, "Development of cancer immunotherapy targeting a novel cancer-testis antigen, CDCA1, that highly expresses in lung cancer," *Kibarmakutekimennekikenkyuukai sokai*, 12, p. 34 (2008).

Harao, M., et al., "HLA-A2-restricted CTL epitopes of a novel lung cancer-associated cancer testis antigen, cell division cycle associated 1, can induce tumor-reactive CTL," *Int. J. Cancer*, vol. 123(11, pp. 2616-2625 (Dec. 1, 2008).

Hayama, S., et al., "Activation of CDCA1-KNTC2, Members of Centromere Protein Complex, Involved in Pulmonary Carcinogenesis," *Cancer Research*, vol. 66(21), pp. 10339-10348 (Nov. 1, 2006).

Hayama, S., et al., "Isolation and characterization of a novel cancer-testis antigen IMS-CL54 that is frequently up-regulated in non-small cell lung cancer," *Nihon Garioakkaisokai, Sixty-Third Annual Meeting of the Japanese Cancer Association*, p. 54, Abstract #W-072 (2004).

Kikuchi, T., et al., "Expression profiles of non-small cell lung cancers on cDNA microarrays: Identification of genes for prediction of lymph-node metastasis and sensitivity to anti-cancer drugs," *Oncogene*, vol. 22(14), pp. 2192-2205 (Apr. 10, 2003).

Kondo, A., et al., "Prominent Roles of Secondary Anchor Residues in Peptide Binding to HLA-A24 Human Class I Molecules," *J. Immunol.*, vol. 155(9), pp. 4307-4312 (Nov. 1, 1995).

Kubo, R,. et al., "Definition of Specific Peptide Motifs for Four Major HLA-A Alleles," *J. Immunol.*, vol. 152(8), pp. 3913-3924 (Apr. 15, 1994).

Liu, S-T., et al., "Mapping the assembly pathways that specify formation of the trilaminar kinetochore plates in human cells," *J. Cell Biol.*, vol. 175(1), pp. 41-53 (Oct. 9, 2006).

Liu, D., et al., "Human NUF2 Interacts with Centromere-associated Protein E and Is Essential for a Stable Spindle Microtubule-Kinetochore Attachment," *J. Biol. Chem.*, vol. 282(29), pp. 21415-21424 (Jul. 20, 2007).

Ruben, S., et al., Database printout from IBIS—Integrated Biotechnological Information Services: GSP:AAG74867 (2001).

Suzuki, C., et al., "Identification of COX17 as a Therapeutic Target for Non-Small Cell Lung Cancer," *Cancer Research*, vol. 63(21), pp. 7038-7041 (Nov. 1, 2003).

Wigge, P., et al., "The Ndc8Op Complex from *Saccharomyces cerevisiae* Contains Conserved Centromere Components and Has a Function in Chromosome Segregation," *J. Cell Biol.*, vol. 152(2), pp. 349-360 (Jan. 22, 2001).

Zaremba, S., et al., "Idenfification of an Enhancer Agonist Cytotoxic T Lymphocyte Peptide from Human Carcinoembryonic Antigen," *Cancer Res.*, vol. 57(20), pp. 4570-4577 (Oct. 15, 1997).

Barnea, et al., GenBank: AAY06266.1, (http://www.ncbi.nlm.nih.gov/protein/AAY06266), 1 page, retrieved May 10, 2012 (Apr. 20, 2005).

U.S. Appl. No. 13/080,461, filed Apr. 5, 2011, 75 pages.

Belli, et al. "Vaccination of Metastatic Melanoma Patients with Autologous Tumor-Derived Heat Shock Protein gp96-Peptide complexes: Clinical and Immunologic Findings," *J Clin Oncol.*, vol. 20(20), pp. 4169-4180 (Oct. 15, 2002).

Boon, "Tumor Antigens Recognized by Cytolytic T Lymphocytes: Present Perspectives for Specific Immunotherapy," *Int J Cancer*, vol. 54(2), pp. 177-180 (May 8, 1993).

Boon, et al., "Human Tumor Antigens Recognized by T Lymphocytes," *J Exp Med.* vol. 183(3), pp. 725-729 (Mar. 1, 1996).

Butterfield, et al., "Generation of Human T-cell Responses to an HLA-A2.1-restricted Peptide Epitope Derived from α-Fetoprotein," *Cancer Res.*, vol. 59(13), pp. 3134-3142 (Jul. 1, 1999).

Coulie, et al., "Cytolytic T-cell responses of cancer patients vaccinated with a MAGE antigen," *Immunol Rev.*, vol. 188, pp. 33-42 (Oct. 2002).

Dionne, et al., "Functional characterization of CTL against gp100 altered peptide ligands," *Cancer Immunol Immunother.*, vol. 52(4), pp. 199-206 (Apr. 2003, Epub Feb. 18, 2003).

Dionne, et al., "Her-2/*neu* altered peptide ligand-induced CTL responses: implications for peptides with increased HLA affinity and T-cell-receptor interaction," *Cancer Immunol Immunother.*, vol. 53(4), pp. 307-314 (Apr. 2004, Epub Nov. 5, 2003).

Falk, et al., "Allele-specific motifs revealed by Sequencing of self-peptide eluted from MHC molecules," *Nature*, vol. 351(6324), pp. 290-296 (May 23, 1991).

Fujie, et al., "A Mage-1-Encoded HLA-A24-Binding Synthetic Peptide Induces Specific Anti-Tumor Cytotoxic T Lymphocytes," *Int J Cancer* vol. 80(2), pp. 169-172 (Jan. 18, 1999).

Harris, Structure and Function of the p53 Tumor Suppressor Gene: Clues for Rational Cancer Therapeutic Strategies, *J Natl Cancer Inst.*, vol. 88(20), pp. 1442-1455 (Oct. 16, 1996).

Hayama, et al., "Isolation and characterization of novel cancer-testis antigens IMS-CL54 and IMS-CL81 that is frequently up-regulated in non-small cell lung cancer," *Nihongangakkai Shoroku*, W-344, p. 240 (Aug. 2005).

Hayama, et al., "Characterization of cancer-testis antigens IMS-CL54 and IMS-CL81 that play a role in lung cancer growth and their therapeutic application," *Nihongangakkai Shoroku*, P-237, p. 157 (2006).

Hayama, et al., "Activation IMS-CL54 and IMS-CL81 complex as promising therapeutic targets for lung cancer," *Proceedings of the American Association for Cancer Research (AACR)*, vol. 47, #2587, p. 610 (2006).

Hoffman, et al., "The Ability of Variant Peptides to Reverse the Nonresponsiveness of T Lymphocytes to the Wild-Type Sequence $p53_{264-272}$Epitope," *J Immunol.*, vol. 168(3), pp. 1338-1347 (Feb. 1, 2002).

Hori, et al., "Dynamic behavior of Nuf2-Hec1 complex that localizes to the centrosome and centromere and is essential for mitotic progression in vertebrate cells," *J Cell Sci.*, vol. 116(Pt 16), pp. 3347-3362 (EPUB Jun. 26, 2003, Aug. 15, 2003).

Ishizaki, et al., "Inhibition of Tumor Growth with Antiangiogenic Cancer Vaccine Using Epitope Peptides Derived from Human Vascular Endothelial Growth Factor Receptor 1," *Clin Cancer Res.*, vol. 12(19), pp. 5841-5849 (Oct. 1, 2006).

Kakiuchi, et al., "Genome-Wide Analysis of Organ-Preferential Metastasis of Human Small Cell Lung Cancer in Mice," *Mol Cancer Res.*, vol. 1(7), pp. 485-499 (May 2003).

Kikuchi, et al., "Identification of a Sart-1-Derived Peptide Capable of Inducing HLA-A24-Restricted and Tumor-Specific Cytotoxic T Lymphocytes," *Int J Cancer*, vol. 81(3), pp. 459-466 (May 5, 1999).

Oiso, et al., "A Newly Identified *Mage*-3-Derived Epitope Recognized by HLA-A24-Restricted Cytotoxic T Lymphocytes," *Int J Cancer*, vol. 81(3), pp. 387-394 (May 5, 1999).

Rammensee, et al., "MHC ligands and peptide motifs: first listing," *Immunogenetics*, vol. 41(4), pp. 178-228 (1995).

Rosenberg, et al., "Cancer immunotherapy: moving beyond current vaccines," *Nat Med.*, vol. 10(9), pp. 909-915 (Sep. 2004).

Tanaka, et al., "Induction of Antitumor Cytotoxic T Lymphocytes with a MAGE-3-encoded Synthetic Peptide Presented by Human Leukocytes Antigen-A24," *Cancer Res.*, vol. 57(20), pp. 4465-4468 (Oct. 15, 1997).

Van Der Burg, et al., "Immunogenicity of Peptides Bound to MHC Class I Molecules Depends on the MHC-Peptide Complex Stability," *J Immunol.*, vol. 156(9), pp. 3308-3314 (May 1, 1996).

Vissers, et al., "The Renal Cell Carcinoma-associated Antigen G250 Encodes a Human Leukocyte Antigen (HLA)-A2.1-restricted Epitope Recognized by Cytotoxic T Lymphocytes," *Cancer Res.* vol. 59(21), pp. 5554-5559 (Nov. 1, 1999).

Walker, "Drug Target Discovery by Gene Expression Analysis: Cell Cycle Genes," *Curr Cancer Drug Targets*, vol. 1(1), pp. 73-83 (May 2001).

Score Search Results Details for U.S. Appl. No. 11/913,142 and Search Result, 2 pages (Feb. 12, 2010).

Score Search Results Details for U.S. Appl. No. 11/913,142 and Search Result, 6 pages (Jun. 3, 2010).

U.S. Appl. No. 13/536,327, filed Jun. 28, 2012, 204 pgs.

U.S. Appl. No. 13/238,273, filed Sep. 21, 2011, 120 pages.

(56) References Cited

OTHER PUBLICATIONS

U.S. Appl. No. 13/246,639, filed Sep. 27, 2011, 164 pages.

Parker et al., "Scheme for Ranking Potential HLA-A2 Binding Peptides Based on Independent Binding of individual Peptide Side-Chains," *J Immunol*. Jan. 1, 1994:152(1): 163-175.

Adams et al., "Prediction of Binding to MHC Class I Molecules," *J Immunol Methods*, Sep. 25, 1995:185(2):181-190.

Schuller-Furman et al., "Structure-Based Prediction of Binding Peptides to MHC Class I Molecules: Application to a Broad Range of MHC Alleles," *Protein Sci*. 2000, Sept.: 9(9): 1838-1846.

Roitt et al., "Immunology" Translation from English-Moscow:Mir. 2000, Fifth Ed., p. 159-62.

Roitt et al., "Immunology" Translation from English-Moscow:Mir. 2000, Fifth Ed., p. 194, 196-199.

Database Genseq. ADS11001, 1 page, 2007.

* cited by examiner

```
SEQUENCE LISTING

<160> NUMBER OF SEQ ID NOS: 41

<210> SEQ ID NO 1
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 1

Tyr Met Met Pro Val Asn Ser Glu Val
1               5

<210> SEQ ID NO 2
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 2

Lys Leu Ala Thr Ala Gln Phe Lys Ile
1               5

<210> SEQ ID NO 3
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 3

Phe Leu Ser Gly Ile Ile Asn Phe Ile
1               5

<210> SEQ ID NO 4
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 4

Arg Leu Asn Glu Leu Lys Leu Leu Val
1               5

<210> SEQ ID NO 5
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 5
```

```
Gln Leu Ser Asp Gly Ile Gln Glu Leu
1               5

<210> SEQ ID NO 6
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 6

Phe Leu Trp Gln Tyr Lys Ser Ser Ala
1               5

<210> SEQ ID NO 7
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 7

Thr Leu Ser Phe Pro Arg Tyr Asn Val
1               5

<210> SEQ ID NO 8
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 8

Cys Leu Pro Ser Cys Gln Leu Glu Val
1               5

<210> SEQ ID NO 9
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 9

Ala Val Tyr Glu Arg Val Thr Thr Ile
1               5

<210> SEQ ID NO 10
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 10

Thr Val Ile Glu Asp Cys Asn Lys Val
1               5

<210> SEQ ID NO 11
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 11

Lys Ile Val Asp Ser Pro Glu Lys Leu
1               5
```

```
<210> SEQ ID NO 12
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 12

Lys Met Lys Asp Thr Val Gln Lys Leu
1               5

<210> SEQ ID NO 13
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 13

Leu Val Thr His Leu Asp Ser Phe Leu
1               5

<210> SEQ ID NO 14
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 14

Lys Ile Asp Glu Lys Thr Ala Glu Leu
1               5

<210> SEQ ID NO 15
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 15

Lys Ile Asn Lys Lys His Glu Asp Val
1               5

<210> SEQ ID NO 16
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 16

Lys Leu Lys Ser Gln Glu Ile Phe Leu
1               5

<210> SEQ ID NO 17
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 17

Phe Leu Pro Phe Ser Asn Leu Val Thr
1               5
```

```
<210> SEQ ID NO 18
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 18

Leu Met Ile Val Lys Lys Glu Lys Leu
1               5

<210> SEQ ID NO 19
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 19

Ile Leu Cys Pro Lys Ala Lys Arg Thr
1               5

<210> SEQ ID NO 20
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 20

Val Leu His Met Ile Tyr Met Arg Ala
1               5

<210> SEQ ID NO 21
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 21

Leu Leu Val Val Ser Leu Lys Glu Ile
1               5

<210> SEQ ID NO 22
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 22

Lys Leu Leu Val Val Ser Leu Lys Glu Ile
1               5                   10

<210> SEQ ID NO 23
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 23

Arg Leu Asn Glu Leu Lys Leu Leu Val Val
1               5                   10

<210> SEQ ID NO 24
<211> LENGTH: 10
```

```
<212> TYPE: PRT
<213> ORGANISM: Artificial
<220> FEATURE:
<223> OTHER INFORMATION: An artificially synthesized peptide sequence

<400> SEQUENCE: 24

Gln Leu Tyr Gln Lys Lys Ile Gln Asp Leu
1               5                   10

<210> SEQ ID NO 25
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 25

Asn Leu Val Thr His Leu Asp Ser Phe Leu
1               5                   10

<210> SEQ ID NO 26
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 26

Lys Gln Leu Ser Asp Gly Ile Gln Glu Leu
1               5                   10

<210> SEQ ID NO 27
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 27

Met Ile Tyr Met Arg Ala Leu Gln Ile Val
1               5                   10

<210> SEQ ID NO 28
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 28

Lys Leu Gly Ile Gln Gln Leu Lys Asp Ala
1               5                   10

<210> SEQ ID NO 29
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 29

Arg Leu Met Ile Val Lys Lys Glu Lys Leu
1               5                   10

<210> SEQ ID NO 30
<211> LENGTH: 10
<212> TYPE: PRT
<213> ORGANISM: Artificial
```

```
<220> FEATURE:
<223> OTHER INFORMATION: An artificially synthesized peptide sequence

<400> SEQUENCE: 30

Lys Leu Ala Ser Ile Leu Lys Glu Ser Leu
1               5                   10

<210> SEQ ID NO 31
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 31

Ile Leu Thr Gly Ala Asp Gly Lys Asn Leu
1               5                   10

<210> SEQ ID NO 32
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 32

Ser Leu Asn Gln Asp Phe His Gln Lys Thr
1               5                   10

<210> SEQ ID NO 33
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 33

Ala Leu Gln Ile Val Tyr Gly Ile Arg Leu
1               5                   10

<210> SEQ ID NO 34
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 34

Val Leu His Met Ile Tyr Met Arg Ala Leu
1               5                   10

<210> SEQ ID NO 35
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 35

Asp Leu Tyr Pro Asn Pro Lys Pro Glu Val
1               5                   10

<210> SEQ ID NO 36
<211> LENGTH: 10
<212> TYPE: PRT
<213> ORGANISM: Artificial
<220> FEATURE:
<223> OTHER INFORMATION: An artificially synthesized peptide sequence
```

```
<400> SEQUENCE: 36

Lys Leu Glu Arg Leu Asp Ser Val Pro Val
1               5                   10

<210> SEQ ID NO 37
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 37

Tyr Met Met Pro Val Asn Ser Glu Val Met
1               5                   10

<210> SEQ ID NO 38
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 38

Gln Leu Asn Ala Ala His Gln Glu Ala Leu
1               5                   10

<210> SEQ ID NO 39
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 39

Arg Leu Glu His Phe Tyr Met Met Pro Val
1               5                   10

<210> SEQ ID NO 40
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 40

Leu Met Ile Val Lys Lys Glu Lys Leu Ala
1               5                   10

<210> SEQ ID NO 41
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 41

Ala Glu Leu Lys Arg Lys Met Phe Lys Met
1               5                   10
```

CDCA1 PEPTIDE AND PHARMACEUTICAL AGENT COMPRISING THE SAME

CROSS-REFERENCES TO RELATED APPLICATIONS

The present application is a U.S. National Phase of PCT/JP2008/060837, filed Jun. 13, 2008, which claims the benefit of Japanese Application No. 2007-214000, filed on Aug. 20, 2007, the disclosures of which are hereby incorporated herein by reference in their entirety.

TECHNICAL FIELD

The present invention relates to novel peptides that are effective as vaccines against cancers which highly express cell division cycle associated 1 (CDCA1), such as lung cancer and cholangiocellular carcinoma, and pharmaceuticals that include these peptides for treatment and prevention of tumors.

BACKGROUND ART

In recent years, the number of lung cancer patients continues to increase all around the world, and approximately one million people are currently dying of lung cancer worldwide each year. Also in Japan, lung cancer deaths are increasing, and estimated to reach 123,000 in 2015. Lung cancer is more prevalent among males, and the male-female ratio is three to one. Lung cancer surpassed stomach cancer in 1993 to be the leading cause of cancer death among males. Furthermore, with an increasing number of female smokers, the number of female patients is expected to rise. Lung cancer has been the leading cause of cancer death since 2000, and with the aging society, the number of patients is expected to increase further in the future. Smoking is considered to be the greatest cause of lung cancer development, and other causes are inhalation of asbestos, air pollution, and such. Early detection and prompt treatment are important for lung cancer therapy. However, it has been recently pointed out that simple chest X-ray and sputum test performed during a medical examination are not effective for early detection of lung cancer, and they do not lead to reduction of cancer deaths. Since the number of lung cancer deaths is expected to continue rising in the future, it is an urgent task to develop new therapeutic strategies.

In Japan, the number of biliary tract cancer deaths is on the rise, and in 2005, 16,586 people died of biliary tract cancer. In most biliary tract cancer cases, no subjective symptoms are found in the early stages. Compared to cancers that form in the digestive tract lumen, such as stomach cancer and colon cancer, biliary tract cancer is difficult to find and diagnose at the early stages. Therefore, in many cases, the cancer has already progressed and is unresectable when it is found. In addition to surgical therapy, radiation therapy and chemotherapy are performed for biliary tract cancer, but they are not therapeutically effective, and it is necessary to establish new therapeutic method.

On the other hand, recent development in molecular biology and tumor immunology has elucidated that cytotoxic (killer) T cells and helper T cells recognize peptides generated by degradation of proteins that are specifically and highly expressed in cancer cells, and which are presented on the surface of cancer cells or antigen presenting cells via HLA molecules and cause immunoreaction to destroy cancer cells. Furthermore, many tumor antigen proteins and peptides derived therefrom, which stimulate such immunoreaction to attack cancer, have been identified, and antigen-specific tumor immunotherapy is being clinically applied.

The HLA class I molecule is expressed on the surface of all nucleated cells of the body. It binds to a peptide generated by intracellular degradation of proteins produced in the cytoplasm or nucleus, and expresses the peptide on the cell surface. On the surface of a normal cell, peptides derived from normal autologous proteins bind to HLA class I molecules, and are not recognized and destroyed by T cells of the immune system. On the other hand, in the process of becoming a cancer, cancer cells sometimes express a large quantity of proteins that are hardly or slightly expressed in normal cells. When HLA class I molecules bind to peptides generated by intracellular degradation of proteins specifically and highly expressed in cancer cells, and then express the peptides on the surface of cancer cells, cytotoxic (killer) T cells recognize and destroy only the cancer cells. By administering such cancer-specific antigens or peptides to an individual, cancer cells can be destroyed and cancer growth can be suppressed without harming normal cells. This is called cancer immunotherapy using cancer-specific antigens. HLA class II molecules are mainly expressed on the surface of antigen-presenting cells. The molecules bind to peptides derived from cancer-specific antigens, which are generated by intracellular degradation of cancer-specific antigens incorporated into antigen-presenting cells from outside of the cells, and then express the peptides on the surface of the cells. Helper T cells that recognize them are activated, and induce or enhance immunoreaction against tumors by producing various cytokines that activate other immunocompetent cells.

Accordingly, if an immunotherapy that targets antigens specifically and highly expressed in cancers is developed, such a therapy can effectively eliminate cancers alone without causing any harmful event on normal autologous organs. It is also expected that the therapy can be used for any terminal cancer patients to whom other treatments cannot be applied. In addition, by administering a cancer-specific antigen and peptide as a vaccine in advance to individuals with a high risk of developing cancers, cancer development can be prevented.

Although there are various therapeutic methods for lung cancer, the lung cancer results in poor prognosis compared to other cancers, and it is one of the intractable cancer. The reason is, for example, rapid progression, and in many cases, the cancer has advanced by the time it is found. Furthermore, since the surgery is highly invasive, patients who is applicable with the surgery are limited, and complete cure by radiation therapy or chemotherapy is difficult. If an immunotherapy targeting antigens that are highly and specifically expressed in lung cancer is developed, cancer alone can be effectively eliminated by such therapeutic method without any damage on the normal autologous organs. Furthermore, such therapeutic method is expected to be applicable to any terminal cancer patient, and patients who are not applicable with other treatments due to extremely poor lung function. In addition, since the risk for lung cancer development is high among smokers, immunotherapy may be applicable for prevention of lung cancer in a high-risk group of lung cancer.

By genome-wide gene expression analysis using cDNA microarrays, the present inventors examined the expression profile of 27,648 human genes in 37 clinical cases of non-small-cell lung cancer and in embryonic organs, and various normal adult organs. As a result, the inventors found that CDCA1 (cell division cycle associated 1, also known as human homologues of Nuf2 (hNuf2)) (GenBank Accession No. NM_145697) was highly expressed in many lung cancer cases, while it was hardly expressed in the embryonic liver or normal adult organs except in the testis isolated from the immune system. Furthermore, CDCA1 was highly expressed in all cases of cholangiocellular carcinoma, bladder cancer, and renal cell carcinoma. High CDCA1 expression was also observed in the cancer tissues of 40% or more cases of prostate cancer, chronic myelogenous leukemia, malignant lymphoma, cervical cancer, osteosarcoma, breast cancer, soft tissue sarcoma, and colon cancer. This fact suggests that CDCA1 could serve as a cancer-specific antigen in many carcinomas.

HLA-A2 is frequently observed in human populations regardless of the race, and is possessed by about 30% of the Japanese. Therefore, if one can identify a cancer antigen peptide that is presented to cytotoxic (killer) T cells by HLA-A2, it can be widely applied to not only the Japanese but also Caucasians and such. Accordingly, it is an important task to identify cancer antigen peptides that are presented to killer T cells by HLA-A2. It would be highly beneficial if such cancer antigen peptides are applicable to immunotherapy for lung cancer, which have high morbidity and mortality all over the world.

Prior art documents related to the present invention are shown below.

[Non-patent document 1] DeLuca J. G., Moree, B., Hickey, J. M., Kilmartin, J. V., and Salmon, E. D., hNuf2 inhibition blocks stable kinetochore-microtubule attachment and induces mitotic cell death in HeLa cells J. Cell Biol. 159: 549-555, 2002.

[Non-patent document 2] DeLuca, J. G., Dong, Y., Hergert, P, Strauss, J., Hickey, J. M., Salmon, E. D., McEwen, B. F., Hec1 and Nuf2 Are Core Components of the Kinetochore Outer Plate Essential for Organizing Microtubule Attachment Sites., Mol. Biol. Cell 16: 519-531, 2005.

[Non-patent document 3] Hayama, S., Daigo, Y., Kato, T., Ishikawa, N., Yamabuki, T., Miyamoto, M., Ito, T., Tsuchiya, E., Kondo, S., and Nakamura, Y, Activation of CDCA1-KNTC2, Members of Centromere Protein Complex, Involved in Pulmonary Carcinogenesis., Cancer Res. 66: 10339-10348, 2006.

[Non-patent document 4] Liu, S. T., Rattner, J. B., Jablonski, S. A., and Yen, T. J., Mapping the assembly pathways that specify formation of the trilaminar kinetochore plates in human cells., J. Cell Biol. 175: 41-53, 2006.

[Non-patent document 5] DeLuca, J. G., Howell, B. J., Canman, J. C., Hickey, J. M., Fang, G., and Salmon, E. D., et al. Nuf2 and Hec1 Are Required for Retention of the Checkpoint Proteins Mad1 and Mad2 to Kinetochores., Current Biology 13: 2103-2109, 2003.

[Non-patent document 6] Liu, D., Ding, D., Du, J., Cai, Xin., Huang, Y., Ward, T., Shaw, A., Yang, Y, Hu, R., Jin, C., and Yao, X., Human NUF2 Interacts with Centromere-associated Protein E and Is Essential for a Stable Spindle Microtubule-Kinetochore Attachment. J. Biol. Chem. 282: 21415-21424, 2007.

DISCLOSURE OF THE INVENTION

Problems to be Solved by the Invention

An objective to be achieved by the present invention is to develop means for implementing immunotherapy that suppresses cancer growth by enhancing the immunity of cancer patients against cancer, as a therapeutic method for metastatic or intractable cancers which are difficult to be treated by surgical therapy, chemotherapy, and radiotherapy for treating lung cancer, biliary tract cancer, etc. The present inventors identified peptides that are derived from proteins specifically and highly expressed in cancer, and which are presented to killer T cells by HLA-A2, thereby enabling immunotherapy to be applicable to about 30% of Japanese patients with various cancers that highly express CDCA1.

Means for Solving the Problems

The present inventors identified the CDCA1 gene (GenBank Accession No. NM_145697), which is highly expressed in lung cancer, from cDNA microarray analysis of lung cancer tissues. CDCA1 expression in normal tissues is observed only in the testis isolated from the immune system. In order to examine whether or not anti-tumor immunity is induced by CDCA1 specific killer T cells, HLA-A2 transgenic mice expressing HLA-A2 which is possessed by approximately 30% of the Japanese were used. Specifically, herein, the inventors examined whether or not HLA-A2 restricted peptide-specific killer T cells are induced when HLA-A2 transgenic mice are immunized with mouse bone marrow-derived dendritic cells pulsed with human CDCA1 peptides having an HLA-A2 binding motif. Whether CDCA1 peptide-specific killer T cells are induced in the spleen cells of immunized mice or not was examined using ELISPOT assay to detect γ-interferon (IFN-γ) produced by killer T cells activated from recognizing peptides presented by HLA-A2. As a result, two types of novel CDCA1 peptides that can be applied to immunotherapy targeting HLA-A2 positive cancer patients were identified. Furthermore, it was confirmed that cancer patient-derived and healthy donor-derived CTLs activated by these peptides show cytolytic activity against CDCA1 expressing cells. That is, the peptides are expected to be recognized by HLA-A2 restricted human killer T cells and applicable to cancer immunotherapy for HLA-A2 positive cancer patients.

More specifically, the present invention provides the following:

[1] a peptide of (A) or (B) below:
(A) a peptide including the amino acid sequence of SEQ ID NO: 1 or 2;
(B) a peptide which includes the amino acid sequence of SEQ ID NO: 1 or 2, wherein one, two, or several amino acid(s) are substituted, deleted, inserted, and/or added, and wherein the peptide shows cytotoxic (killer) T cell-inducing activity;

[2] the peptide of [1], wherein the second amino acid from the N terminus is leucine or methionine;

[3] the peptide of [1], wherein the C-terminal amino acid is valine or leucine;

[4] an agent for inducing immunity against cancer, which includes one or more peptide(s) of [1] as an active ingredient;

[5] an agent for treating and/or preventing cancer, which includes one or more peptide(s) of [1] as an active ingredient;

[6] an agent for inducing an antigen-presenting cell that shows cytotoxic (killer) T cell-inducing activity, wherein said agent includes one or more peptide(s) of [1] as an active ingredient;

[7] an agent for inducing an antigen-presenting cell that shows cytotoxic (killer) T cell-inducing activity, wherein said agent includes one or more polynucleotide(s) encoding the peptides of [1] as an active ingredient;

[8] an agent for inducing a cytotoxic (killer) T cell, wherein said agent includes one or more peptide(s) of [1] as an active ingredient;

[9] an antibody against the peptide of [1];

[10] a helper T cell, a cytotoxic (killer) T cell, or an immunocyte population including them, which is induced using the peptide of [1];

[11] an antigen-presenting cell that presents a complex including the peptide of [1] and an HLA antigen;

[12] the antigen-presenting cell of [11], which is induced by the agent of [6] or [7];

[13] an exosome that presents a complex including the peptide of [1] and an HLA antigen;

[14] the exosome of [13], wherein the HLA antigen is HLA-A2 (HLA-A2*0201);

[15] a method for inducing an antigen-presenting cell that shows cytotoxic (killer) T cell-inducing activity, which includes the step of contacting an antigen-presenting cell with the peptide of [1];

[16] a method for inducing an antigen-presenting cell that shows cytotoxic (killer) T cell-inducing activity, which includes the step of introducing a polynucleotide encoding the peptide of [1] into an antigen presenting cell;

[17] a method for inducing a cytotoxic (killer) T cell, which includes the step of contacting a T cell with the peptide of [1];

[18] a method for inducing immunity against cancer, which includes the step of administering the peptide of [1] to a subject;

[19] a method for treating and/or preventing cancer, which includes the step of administering the peptide of [1] to a subject;

[20] use of the peptide of [1] for the production of an agent for inducing immunity against cancer;

[21] use of the peptide of [1] for the production of an agent for treating and/or preventing cancer;

[22] the peptide of [1], for induction of immunity against cancer;

[23] the peptide of [1], for treatment and/or prevention of cancer.

BRIEF DESCRIPTION OF THE DRAWINGS

FIG. 2A shows the result of killer T cell induction by stimulation with $CDCA1_{65-73}$ (No. 1) (SEQ ID NO: 1) peptide-pulsed dendritic cells derived from the bone marrow of HLA-A2 transgenic mice. When CDCA1 peptide-pulsed T2A2 cells were used as the stimulator cells, the spot count and total spot area were significantly greater than those when HLA-A2 positive non-CDCA1 pulsed T2A2 cells were used as the stimulator cells. Thus, it was determined that the CDCA1-1 peptide is an epitope peptide capable of inducing HLA-A2 restricted killer T cells. FIG. 2B shows the result of killer T cell induction by stimulation with $CDCA1_{351-359}$ (No. 4) (SEQ ID NO: 2) peptide-pulsed dendritic cells derived from the bone marrow of HLA-A2 transgenic mice. When CDCA1 peptide-pulsed T2A2 cells were used as the stimulator cells, the spot count and total spot area were significantly greater than those when HLA-A2 positive non-CDCA1 pulsed T2A2 cells were used as the stimulator cells. Thus, it was determined that the $CDCA1_{351-359}$ (No. 4) peptide is an epitope peptide capable of inducing HLA-A2 restricted killer T cells.

FIG. 3A shows the protocol for induction of CDCA1 specific CTLs from PBMCs. PBMCs were isolated from a healthy donor, and $CD8^+$ T cells and $CD14^+$ cells were separated using microbeads. Then, peptide-reactive $CD8^+$ CTLs were produced, and DCs were produced from CD14 positive cells by culturing for five days in the presence of GM-CSF and IL-4. DCs were cultured in the presence of β2 microglobulin at 37° C. for four hours, and pulsed with HLA-A2 binding peptides. The peptide-pulsed DCs were then irradiated and mixed with autologous CD8 positive T cells at 1:20 ratio. Cells were cultured in AIM-V containing 2% autoserum supplemented with IL-7. After three days, IL-2 was added to the culture medium. On days 12 and 19, the T cells were restimulated with peptide-pulsed autologous DCs. The DCs were prepared upon use. IFN-γ ELISPOT assay and Cr release assay were performed five and six days after the third peptide stimulation. FIGS. 3B and C show the results of ELISPOT assay performed after coculturing target cells with CTLs induced from a donor using the $CDCA1_{65-73}$ (No. 1) peptide and the $CDCA1_{351-359}$ (No. 4) peptide, respectively. The IFN-γ production against peptide-pulsed T2 cells was significantly higher than that against non-peptide-pulsed T2 cells. FIG. 3D shows the cytotoxicity of CTLs induced from PBMCs of cancer patient donor 1 and healthy donor 1 against CDCA1 peptide-pulsed T2 cells. FIG. 3E shows the dose-dependent response of healthy donor 1-derived CTLs induced by the $CDCA1_{351-359}$ peptide. The CTLs produced a large amount of IFN-γ in response to T2 cells pulsed with the peptide at 0.2 μg/mL or more at an E/T ratio of 5.

FIG. 4A shows the expression in COLO201 cells when a CDCA1 gene expression vector was introduced into the cells. A lentivirus in which the CDCA1-HA expression is induced under the EF-1α promoter and CMV promoter was used to infect the cancer cell line (COLO201), which expresses HLA-A2 but not CDCA1, three times. The cell lysate was subjected to Western blot analysis using an anti-HA antibody (middle) or anti-CDCA1 antibody (upper). FIGS. 4B, C, and D show the IFN-γ production against COLO201/CDCA1. The IFN-γ production was significantly higher for a transformed COLO201 cancer cell line than for untransformed COLO201. Furthermore, the IFN-γ production against PANC1 endogenously expressing both CDCA1 and HLA-A2 was significantly greater than that against A549 expressing neither CDCA1 or HLA-A2. FIGS. 4E and F show the results of $^{51}Cr$ release assay when donor-induced CTLs and target cells were co-cultured. The cytotoxicity was observed for PANC1 (CDCA1+, HLA-A2+), but not for A549 (CDCA1+, HLA-A2−) and COLO201 (CDCA1−, HLA-A2+). FIG. 4G shows the correlation between the CDCA1 peptide-reactive CTLs and the HLA-A2-CDCA1 tetramer positive CTLs among CD8 positive cells. The left diagram shows the ELISPOT assay using peptide-pulsed T2 cells as the target cells, and the E/T ratio was 5. The right diagram shows the result of FACS analysis. The cells analyzed in the left diagram are healthy donor 1-derived CTLs subjected to three times of PBMC stimulation with peptide-pulsed DCs. The cells analyzed in the right diagram are naive CD8 positive cells separated from PBMCs of healthy donor 1.

MODE FOR CARRYING OUT THE INVENTION

Figure 1:
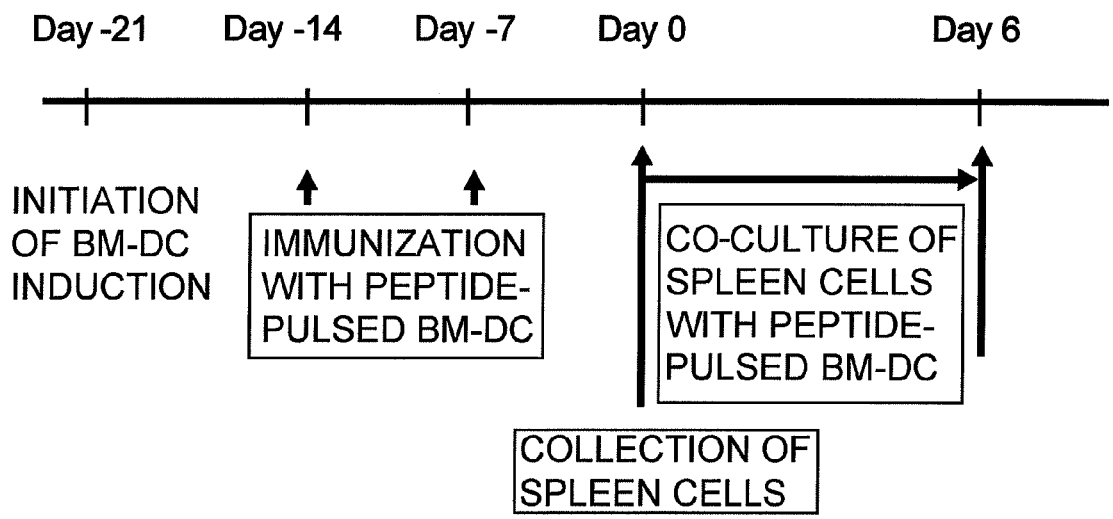
FIG. 1A shows the protocol for identifying CDCA1 peptides recognized by HLA-A2 restricted killer T cells. The day when spleen cells were collected from immunized mice is designated as "Day 0".
FIG. 1B shows the ELISPOT assay results. ELISPOT assay was used to examine whether or not killer T cells obtained from immunized mice respond specifically to CDCA1 peptide-pulsed cells and produce IFN-γ. As a result, killer T cells induced with the CDCA1-1 or CDCA1-4 peptide specifically recognized CDCA1 peptide-pulsed T2A2 cells and produced IFN-γ. However, no CDCA1 specific killer T cell immune response was observed in killer T cells induced with other peptides. Therefore, it was determined that the CDCA1-1 and CDCA1-4 peptides are epitope peptides capable of inducing CDCA1 specific HLA-A2 restricted killer T cells. The numbers of the CDCA1 peptide shown in FIG. 1B correspond to the peptide numbers shown under "PEPTIDE POSITION" of Table 1, but not to the sequence ID numbers described herein.
Figure 1:
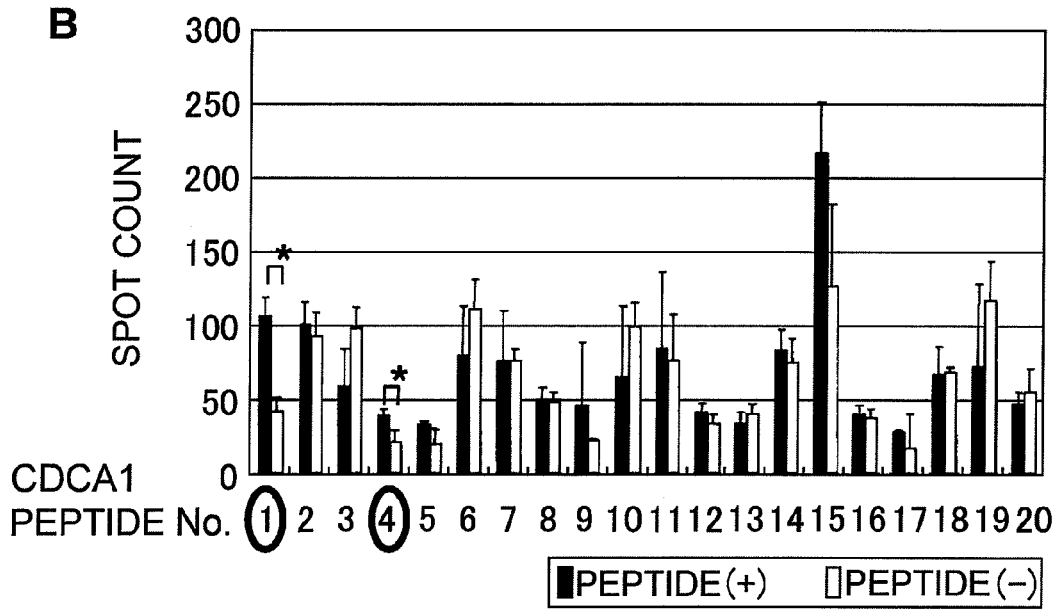

Unless otherwise defined, all technical and the scientific terms used herein have the same meaning as commonly understood by one of ordinary skill in the art to which the present invention belongs.

The peptides of the present invention are epitopes restricted to HLA-A2, which is an HLA allele frequently found in the Japanese and Caucasian populations. Specifically, using the binding affinity to HLA-A2 as an index, candidate HLA-A2 binding peptides derived from CDCA1 were selected. For the selected peptides, whether or not killer T cells were induced in the body of HLA-A2 transgenic mice by HLA-A2 transgenic mouse bone marrow cell-derived dendritic cells (BM-DCs) pulsed with the selected peptides was evaluated. Cytotoxic (killer) T cells were induced in vivo in HLA-A2 transgenic mice by CDCA1-1 (YMMPVNSEV (SEQ ID NO: 1)) and CDCA1-4 (KLATAQFKI (SEQ ID NO: 2)). Killer T cells induced by these peptides showed immune response reaction to T2A2 cells pulsed with these peptides. However, these killer T cells did not show immune response reaction to non-peptide-pulsed T2A2 cells. Furthermore, cancer patient-derived and healthy donor-derived CTLs that were induced using CDCA1-1 and CDCA1-4 showed cytolytic activity against cell lines expressing CDCA1. These results demonstrate that the CDCA1 derived peptides are useful as peptides inducing immunoreaction against CDCA1 presenting cells, and that the CDCA1 derived peptides are HLA-A2 restricted epitope peptides. It has been shown that CDCA1 is highly expressed in cancerous tissues in most cases of lung cancer, cholangiocellular carcinoma, bladder cancer, renal cell carcinoma, prostate cancer, chronic myelogenous leukemia, malignant lymphoma, cervical cancer, osteosarcoma, breast cancer, soft tissue sarcoma, and colon cancer. From these facts, CDCA1 is considered to be useful as an immunotherapeutic target for various cancers.

(1) Peptides of the Present Invention and Agents for Inducing Immunity Against Cancer that Contain the Peptides The peptide of the present invention is any one of (A) to (D) below.

(A) A peptide including the amino acid sequence of SEQ ID NO: 1 or 2.

(B) A peptide which includes the amino acid sequence of SEQ ID NO: 1 or 2, wherein one, two, or several amino acids are substituted, deleted, inserted and/or added, and wherein the peptide shows cytotoxic (killer) T cell-inducing activity.

(C) The peptide of (B), wherein the second amino acid from the N terminus is leucine or methionine.

(D) The peptide of (B), wherein the C-terminal amino acid is valine or leucine.

Herein, "a peptide that shows an activity of inducing killer T cells" means "a peptide having T cell-inducing activity that stimulates killer T cells (cytotoxic T cells/CTLs)".

The peptide of the present invention is an epitope peptide having less than about 40 amino acids, preferably less than about 20 amino acids, more preferably less than about 15 amino acids, and including the amino acid sequence of SEQ ID NO: 1 or 2, and showing an activity of inducing killer T cells. Furthermore, the peptides of the present invention (epitope peptides) may include a peptide including the amino acid sequence of SEQ ID NO: 1 or 2, wherein one, two, or several amino acids are substituted, deleted, inserted, and/or added, as long as the ability to induce killer T cells is retained. The number of residues substituted, deleted, inserted, and/or added is generally five amino acids or less, preferably four amino acids or less, more preferably three amino acids or less, even more preferably one amino acid or two amino acids.

Variant peptides (i.e., peptides including amino acid sequences obtained by modifying the original amino acid sequences by substitution, deletion, insertion, and/or addition of one, two, or several amino acid residues) are known to retain the original biological activity (Mark D F et al., (1984) Proc Natl Acad Sci USA 81:5662-6; Zoller M J and Smith M, (1982) Nucleic Acids Res 10:6487-500; Dalbadie-McFarland G et al. (1982) Proc Natl Acad Sci USA 79:6409-13). The amino acid modification preferably retains the properties of the original amino acid side chains. Examples of the properties of amino acid side chains include: hydrophobic amino acid (A, I, L, M, F, P, W, Y, V); hydrophilic amino acid (R, D, N, C, E, Q, H, K, S, T); and side chains having the following functional groups or properties in common: aliphatic side chains (G, A, V, L, I, P); hydroxy group-containing side chains (S, T, Y); sulfur atom-containing side chains (C, M); carboxylic acid- and amide-containing side chains (D, N, E, Q); base-containing side chains (R, K, H); and aromatic ring-containing side chains (H, F, Y, W). The characters in the parentheses show one-character codes of amino acids.

In a preferred embodiment, the peptides of the present invention (immunogenic peptides) are nonapeptides (9-mer) or decapeptides (10-mer).

In order to obtain peptides with high binding affinity and killer T cell-inducing activity, the amino acid sequence of a partial peptide of naturally-occurring CDCA1 may be modified by substitution, deletion, insertion, and/or addition of one, two, or several amino acids. Herein, the term "several" refers to five or less, preferably three or less, more preferably two or less. Furthermore, since the regularity of the peptide sequences that have high affinity to HLA antigens is known (Kubo R T, et al., (1994) J. Immunol., 152, 3913-24; Rammensee H G et al., (1995) Immunogenetics. 41:178-228; Kondo A, et al. (1995) J. Immunol. 155:4307-12), the peptides of the present invention (epitope peptides) can be modified based on the regularity in order to enhance their affinity to HLA antigens. For example, peptides with high HLA-A2 binding affinity can be obtained by substituting the second amino acid from the N terminus with leucine or methionine. Similarly, peptides with high HLA-A2 binding affinity can also be obtained by substituting the C-terminal amino acid with valine or leucine.

When the sequence of an epitope peptide is identical to a portion of the amino acid sequence of an endogenous or exogenous protein having a different function, side effects such as autoimmune disorders or allergy symptoms against a specific substance can be caused. In order to avoid such side effects, a modified epitope peptide should not be identical to the amino acid sequences of known proteins. For this purpose, it is necessary to carry out homology search using available databases to confirm that there is no endogenous or exogenous protein with a different function that shows 100% homology with the modified epitope peptide. By this procedure, risks caused by the above-mentioned amino acid sequence modification for increasing the binding affinity to HLA antigens and/or for increasing the killer T cell-inducing activity can be avoided.

Although the above-mentioned peptides having high binding affinity to HLA antigens are expected to be highly effective as cancer vaccines, candidate peptides selected using high binding affinity as an index need to be examined whether they actually have killer T cell-inducing activity. The killer T cell-inducing activity can be confirmed by: inducing antigen-presenting cells having the human MHC antigen (for example, B lymphocytes, macrophages, and dendritic cells), more specifically, inducing dendritic cells derived from human peripheral blood mononuclear leukocytes; stimulating them with a peptide of interest; then mixing them with CD8 positive cells; and measuring the cytotoxic activity towards target cells. As a reaction system, transgenic animals that express the human HLA antigen (as described in, for example, BenMohamed L, et al. (2000) Hum. Immunol. 61(8):764-79, Related Articles, Books, and Linkout) can be used. For example, to measure the cytotoxic activity, target cells are radiolabeled with $^{51}$Cr or such. The cytotoxic activity on target cells can be examined by measuring IFN-γ produced and released by killer T cells in the presence of the antigen-presenting cells having an immobilized peptide; and visualizing the IFN-γ production zone in the culture medium using an anti-IFN-γ monoclonal antibody.

As shown in the Examples, the result of examining the killer T cell-inducing activity of peptides showed that peptides having high binding affinity to the HLA antigen do not necessarily have high killer T cell-inducing activity. However, the peptides containing the amino acid sequences of CDCA1-1 (YMMPVNSEV (SEQ ID NO: 1)) and CDCA1-4 (KLATAQFKI (SEQ ID NO: 2)) showed particularly high killer T cell-inducing activity.

As described above, the present invention provides peptides showing killer T cell-inducing activity, more specifically, peptides including the amino acid sequence of SEQ ID NO: 1 or 2, and variants thereof (L e., amino acid sequences in which one, two, or several amino acids are substituted, deleted, inserted and/or added). Preferably, the amino acid sequences of the peptides including the nine amino acids of SEQ ID NO: 1 or 2, or variants thereof are not identical to those of other endogenous proteins. Especially, peptides with high HLA-A2 binding affinity can be obtained by substituting the second amino acid from the N terminus with leucine or methionine, and/or by substituting the C-terminal amino acid with valine or leucine.

The peptides of the present invention may include modifications such as glycosylation, side chain oxidation, and phosphorylation, unless the peptides lose their killer T cell-inducing activity. Other modifications include, for example, D-amino acids and other amino acid analogues that can be used to increase the serum half-life of the peptides.

Methods for obtaining and producing the peptides of the present invention are not particularly limited. Chemically synthesized peptides or recombinant peptides produced by gene recombination techniques are available.

Chemically synthesized peptides of the present invention can be synthesized according to chemical synthesis methods such as the Fmoc method (fluorenylmethyloxycarbonyl method) and the t-Boc method (t-butyloxycarbonyl method). The peptides of the present invention can also be synthesized utilizing various commercially-available peptide synthesizers.

The peptides of the present invention can be produced as recombinant proteins by obtaining DNAs having the nucleotide sequences encoding the peptides, or variants or homologs thereof, and introducing them into a suitable expression system.

Expression vectors used may be preferably any vectors that can be autonomously duplicated in host cells, or can be incorporated into the chromosome of host cells, and contain a promoter at a suitable position to allow expression of a peptide-encoding gene. Transformants having a gene encoding the peptide of the present invention can be produced by introducing the above-mentioned expression vector into a host. The host may be any of bacteria, yeast, animal cells, and insect cells, and the expression vector may be introduced into the host using known techniques depending on the host.

In the present invention, the recombinant peptides can be isolated by culturing a transformant prepared as described above, producing and accumulating the peptides in the culture, and collecting the peptides of the present invention from the culture.

When the transformant is a prokaryote such as *E. coli* or an eukaryote such as yeast, the culture medium for these microorganisms may be either natural or synthetic medium, as long as it contains carbon source, nitrogen source, minerals, and such that can be utilized by the microorganisms, and allows efficient culture of the transformant. The culture conditions may be those conventionally used for culturing the microorganisms. After culturing, the peptides of the present invention can be isolated and purified from the culture of the transformant using conventional methods for peptide isolation and purification.

Peptides including an amino acid sequence in which one, two, or several amino acids are substituted, deleted, inserted, or added in the amino acid sequence of SEQ ID NO: 1 or 2 can be appropriately produced or obtained by a person skilled in the art based on the information on the DNA nucleotide sequence encoding the amino acid sequence of SEQ ID NO: 1 or 2. Specifically, a gene that encodes a peptide including an amino acid sequence in which one, two, or several amino acids are substituted, deleted, inserted and/or added in the amino acid sequence of SEQ ID NO: 1 or 2, and showing killer T cell-inducing activity can be produced by any methods known to persons skilled in the art, such as chemical synthesis, genetic engineering techniques, and mutagenesis. For example, the site-directed mutagenesis method, which is one of the genetic engineering techniques, is useful since it can introduce a specific mutation into a specific position. It can be carried out according to the methods described in Molecular Cloning: A laboratory Manual, $2^{nd}$ Ed., Cold Spring Harbor Laboratory, Cold Spring Harbor, N.Y., 1989 (hereinafter referred to as Molecular Cloning, $2^{nd}$ Ed.) and Current Protocols in Molecular Biology, Supplement 1-38, John Wiley & Sons (1987-1997) (hereinafter referred to as Current Protocols in Molecular Biology), etc.

The above-described peptides of the present invention can induce immunity against cancer, as shown below in the Examples. Therefore, the present invention provides agents for inducing immunity against cancer including the peptides of the present invention.

The immunity-inducing agents of the present invention can be prepared as a mixed formulation combined with two or more epitope peptides. Immunity-inducing agents formulated by combining multiple types of peptides may be a cocktail, or may be mutually bound using standard techniques. The epitope peptides to be combined may be peptides having different amino acid sequences derived from the same gene, or may be peptides having amino acid sequences derived from different genes. When the peptides of the present invention are administered, the administered peptides are presented on HLA antigens of antigen-presenting cells at a high density, and subsequently, killer T cells that react specifically to the complexes formed with the administered peptides and the HLA antigens are induced. Alternatively, by contacting dendritic cells collected from a subject with the peptides of the present invention (i.e., by pulsing dendritic cells collected from a subject with the peptides of the present invention), antigen-presenting cells that present the peptides of the present invention on their cell surface can be obtained. By administrating these antigen-presenting cells back to the subject, killer T cells can be induced in the subject's body, and as a result, immune response to target cells presenting the peptides of the present invention can be enhanced.

When used in vitro or in vivo, preferably in vitro, the agents for inducing immunity against cancer of the present invention can induce helper T cells, killer T cells, or immunocyte populations including these cells, thereby providing immunity against cancer.

(2) Agents for Treatment and/or Prevention of Cancer of the Present Invention (Cancer Vaccines)

It was shown in the Examples that the peptides of the present invention can induce cancer cell-specific killer T cells in vivo. On the other hand, it was shown in the previous invention that CDCA1 was highly expressed in most cases of lung cancer, cholangiocellular carcinoma, bladder cancer, renal cell carcinoma, prostate cancer, chronic myelogenous leukemia, malignant lymphoma, cervical cancer, osteosarcoma, breast cancer, soft tissue sarcoma, colon cancer, and such. Accordingly, the immunity-inducing agents including one or more of the peptides of the present invention as an active ingredient are expected to be effective as agents for treatment and/or prevention of cancer. That is, induction and activation of tumor-attacking killer T cells can be expected by injecting the peptides of the present invention together with a suitable adjuvant into the body, or by pulsing antigen-presenting cells such as dendritic cells with the peptides, and then injecting them into the body. Thus, as a result, anticancer effects can be expected. Furthermore, a gene encoding a peptide of the present invention can be incorporated into a suitable vector. Human antigen presenting cells (dendritic cells, etc.) and bacteria such as BCG Mycobacterium tuberculosis that are transformed with the recombinant DNA, or viruses such as vaccinia viruses that have a DNA encoding the peptide of the present invention incorporated into their genome, can be used effectively as live vaccines for treatment and/or prevention of human cancer. The dosages and the administration methods for the cancer vaccines are the same as those for conventional smallpox vaccines and BCG vaccines.

In the present invention, the term "vaccine" (also called "immunogenic composition") refers to a substance that induces antitumor immunity or suppresses various cancers when inoculated to an animal. According to the present invention, it was suggested that the peptide including the amino acid sequence of SEQ ID NO: 1 or 2 is an HLA-A2 restricted epitope peptide that can induce strong and specific immune response against CDCA1 presenting cells. Accordingly, the present invention also includes methods for inducing antitumor immunity by using the peptides including the amino acid sequence of SEQ ID NO: 1 or 2, or variants thereof that include substitution, deletion, or addition of one, two, or several amino acids. In general, the antitumor immunity includes the following immune responses:

(1) induction of killer T cells against tumors containing CDCA1 expressing cells,
(2) induction of antibodies that recognize tumors containing CDCA1 expressing cells, and
(3) induction of antitumor cytokine production.

When a particular peptide induces any one of these immune responses through inoculation to an animal, the peptide is determined to have antitumor immunity-inducing effect. Induction of antitumor immunity by the peptide can be detected by observing in vivo or in vitro response of the immune system in a host to the peptide.

For example, methods for detecting induction of killer T cells are well known. A foreign substance that invades a living body is presented to T cells and B cells by the action of antigen-presenting cells (APCs). T cells that respond to antigens presented by antigen-presenting cells in an antigen-specific manner differentiate into killer T cells (also called cytotoxic T lymphocytes or CTLs) through stimulation by antigens, and then proliferate. Herein, this process is called "activation" of T cells. Induction of killer T cells by a specific peptide can be evaluated by presenting the peptide to T cells using peptide-pulsed antigen-presenting cells, and then detecting the induction of killer T cells. Furthermore, antigen-presenting cells have an effect of activating $CD4^+$ T cells, $CD8^+$ T cells, macrophages, eosinophils, and NK cells. Since $CD4^+$ T cells are also important in antitumor immunity, the antitumor immunity-inducing action of the peptide can be evaluated using the effect on activating these cells as an index.

A method for evaluating the effect of inducing killer T cells that are induced using dendritic cells (DCs) as antigen-presenting cells is well known in the art. Among antigen-presenting cells, DCs have the strongest killer T cell-inducing effect. In this method, first, a test peptide is contacted with DCs, and then the DCs are contacted with T cells. T cells that have cytotoxic effect on target cells are detected from the T cells contacted with DCs. If the T cells show cytotoxic activity against the target cells, it means that the test peptide has the activity to induce cytotoxic T cells. The activity of killer T cells against target cells such as tumors can be detected, for example, using lysis of $^{51}Cr$-labeled tumor cells as an index. Alternatively, the degree of tumor cell damage can be evaluated using $^3H$-thymidine uptake activity or LDH (lactose dehydrogenase) release as an index.

Test peptides confirmed by these methods to have killer T cell-inducing activity are peptides that have DC-activating effect and subsequent killer T cell-inducing activity. Therefore, the peptides that induce killer T cells against tumor cells are useful as vaccines against cancers presenting CDCA1. Furthermore, antigen-presenting cells that have acquired the ability to induce killer T cells against cancers through contact with the peptides are useful as vaccines against cancers. Furthermore, killer T cells that have acquired cytotoxicity as a result of presentation of the peptides by antigen-presenting cells can also be used as vaccines against cancers presenting CDCA1. Methods of cancer treatment using antitumor immunity by antigen-presenting cells and killer T cells are called cytoimmunotherapy.

In general, when using peptides for cytoimmunotherapy, the efficiency of inducing killer T cells can be enhanced by combining multiple peptides having different structures. Therefore, when stimulating DCs with protein fragments, it is advantageous to use a mixture of multiple types of peptide fragments.

Induction of antitumor immunity by peptides can also be evaluated by observing the induction of antibody production against tumors. For example, when antibodies are induced against peptides by immunizing laboratory animals with the peptides, and they suppress growth, proliferation, and/or metastasis of tumor cells, it is determined that the peptides induce antitumor immunity.

Antitumor immunity can be induced by administering a vaccine of the present invention, and the induction of antitumor immunity enables treatment and/or prevention of cancers. Effects of cancer treatment and/or prevention of cancer development may include inhibition of cancer cell growth, regression of cancer cells, and suppression of cancer cell development. Decrease in the mortality rate of individuals with cancer, decrease in tumor markers in blood, and reduction of detectable symptoms associated with cancer are also included in the effects of treatment and/or prevention of cancer. The therapeutic or preventive effects of a vaccine against cancer are preferably statistically significant compared to those of a control without vaccine administration. For example, the effects are preferably observed at a significance level of 5% or less. Statistical methods such as Student t-test, Mann-Whitney U test, and ANOVA may be used for determining the statistical significance.

In the present invention, the subject is preferably a mammal. Examples of mammals include humans, non-human primates, mice, rats, dogs, cats, horses, and cattle, but are not limited hereto.

The peptides of the present invention can be administered to a subject in vivo or ex vivo. Furthermore, to produce an immunogenic composition for treatment and/or prevention of cancer, the immunogenic peptides of the present invention, that is, nonapeptides selected from the amino acid sequences of SEQ ID NOs: 1 and 2, and mutant peptides thereof, may be used.

More specifically, the present invention provides pharmaceutical agents for treatment of tumor and/or prevention of tumor growth, metastasis, and such, which include one or more of the peptides of the present invention as an active ingredient. The peptides of the present invention are particularly useful for treatment of tumors such as lung cancer, cholangiocellular carcinoma, bladder cancer, renal cell carcinoma, prostate cancer, chronic myelogenous leukemia, malignant lymphoma, cervical cancer, osteosarcoma, breast cancer, soft tissue sarcoma, and colon cancer.

The peptides of the present invention can be administered directly to a subject as pharmaceutical agents formulated by conventional formulation methods. Such formulations may contain, in addition to the peptides of the present invention, pharmaceutically acceptable carriers, excipients, and such, as necessary. The pharmaceutical agents of the present invention may be used for treatment and/or prevention of various tumors.

Furthermore, to effectively establish cellular immunity, adjuvants can be mixed into immunogenic compositions for treatment and/or prevention of tumors including one or more of the peptides of the present invention as an active ingredient. The agents may be co-administered with other active ingredients such as antitumor agents. Appropriate formulations also include granules. Appropriate adjuvants are described in the literature (Johnson A G. (1994) Clin. Microbiol. Rev., 7:277-89). Examples of adjuvants include Freund's incomplete adjuvant, BCC, trehalose dimycolate (TDM), lipopolysaccharide (LPS), aluminum potassium sulfate adjuvant, silica adjuvant, aluminum phosphate, aluminum hydroxide, and alum, but are not limited thereto. Furthermore, liposomal formulations, granular formulations in which a drug is bound to beads having a diameter of several micrometers, and formulations in which lipids are bonded to the aforementioned peptides may be conveniently used. Administration methods may be oral administration, intradermal injection, subcutaneous injection, intravenous injection, or such, and may include systemic administration and local administration near the target tumor.

The dose of the peptides of the present invention can be adjusted appropriately depending on the disease to be treated, age and body weight of the patient, administration method, and such. The dose is usually 0.001 mg to 1000 mg, preferably 0.01 mg to 100 mg, and more preferably 0.1 mg to 10 mg. Preferably, administration is performed once a few days to a few months, but those skilled in the art can easily select the appropriate dose and administration method; and selection and optimization of these parameters are fully within the scope of conventional techniques. The form of formulations is not particularly limited, and they may be freeze-dried, or granulated by adding excipients such as sugar.

Auxiliary agents that can be added to the pharmaceutical agents of the present invention for increasing the killer T cell-inducing activity include bacterial components of BCG bacteria and such including muramyl dipeptide (MDP), ISCOM described in Nature, vol. 344, p 873 (1990), QS-21 of saponin series described in J. Immunol. vol. 148, p 1438 (1992), liposome, and aluminum hydroxide. Furthermore, immunostimulants such as lentinan, sizofiran, and picibanil can also be used as auxiliary agents. Cytokines and such that enhance the growth and differentiation of T cells, such as IL-2, IL-4, IL-12, IL-1, IL-6, and TNF, as well as α-galactosylceramide which activates NK T cells, and CpG and lipopolysaccharides (LPS) which activate the natural immune system by binding to Toll-like receptors, and such, can also be used as auxiliary agents.

Vaccine compositions of the present invention contain a component that primes killer T cells. Lipids have been identified as a substance for priming against viral antigens in vivo. For example, palmitic acid residues can be bound to the ε-amino group and α-amino group of a lysine residue, and then linked to an immunogenic peptide of the present invention. The lipidated peptides can be directly administered by incorporating them into a micelle or particle, or encapsulating them into a liposome, or emulsifying them in an adjuvant. Another example of lipid priming is priming with an *E. coli* lipoprotein such as tripalmitoyl-S-glyceryl-cysteinylserylserine (P3CSS) when covalently bound to a suitable peptide (Deres K., et al., (1989) Nature 342:561-4).

The immunogenic peptides of the present invention can be expressed by viral vectors or bacterial vectors. Examples of appropriate expression vectors include avirulent viral hosts such as vaccinia and fowlpox. For example, a vaccinia virus can be used as a vector to express a nucleotide sequence encoding the peptide. By introducing the recombinant vaccinia virus into host cells, the immunogenic peptides are expressed, eliciting immune response. The immunization method using vaccinia vectors is described, for example, in U.S. Pat. No. 4,722,848. Bacille Calmette-Guerin (BCG) may also be used. BCG vectors are described in Stover C K, et al., (1991) Nature 31:456-60. A wide variety of other vectors useful for therapeutic administration or immunization, including adenovirus vectors and adeno-associated virus vectors, retroviral vectors, typhoid bacillus (*Salmonella typhi*) vectors, and detoxified anthrax toxin vectors, are known in the art. See, for example, Shata M T, et al., (2000) Mol. Med. Today 6:66-71; Shedlock D J and Weiner D B., et al., (2000) J. Leukoc. Biol. 68:793-806; and Hipp J D, et al., (2000) In Vivo 14:571-85.

Killer T cells can be effectively induced in the body of a patient by adding an antigenic peptide in vitro to cells collected from the patient or cells from another individual sharing some of the HLA alleles (allogeneic cells), and presenting the antigen, and then administering the cells to the patient intravascularly, locally to the tumor, or such. Alternatively, after in vitro induction of killer T cells by adding the peptide to the patient's peripheral blood lymphocytes and culturing them in vitro, the cells can be administered to the patient intravascularly, locally to the tumor, or such. Such cell transfer treatment has already been carried out as cancer therapy, and is a well-known method among those skilled in the art.

The type of cancers in the present invention is not particularly limited, and specific examples include lung cancer, cholangiocellular carcinoma, bladder cancer, renal cell carcinoma, prostate cancer, chronic myelogenous leukemia, malignant lymphoma, cervical cancer, osteosarcoma, breast cancer, soft tissue sarcoma, colon cancer, etc. Examples of cancers for which application of the present invention is suitable include lung cancer.

(3) Antibodies of the Present Invention

The present invention also relates to antibodies that recognize a portion of or the entire peptide of the present invention mentioned above as an epitope (antigen), and relates to killer T cells that are induced by in vitro stimulation using the proteins or peptides. In general, the killer T cells demonstrate more potent antitumor activity than the antibodies.

Furthermore, similarly to the peptides of the present invention, the antibodies of the present invention are useful as prophylactic and/or therapeutic agents against cancers expressing CDCA1, as long as they can inhibit the activity of the CDCA1 cancer antigen. In a practical use, the peptides or antibodies of the present invention may be administered as they are, or by injection with a pharmaceutically acceptable carrier and/or diluent, together with an adjuvant as necessary. Alternatively, they may be administered by transdermal absorption through mucous membranes by the spray method or such. More specifically, herein, human serum albumin is an example of carriers; and PBS, distilled water, and such are examples of diluents.

The antibodies of the present invention may be polyclonal antibodies or monoclonal antibodies, and can be produced by methods known to those skilled in the art.

For example, polyclonal antibodies can be obtained by immunizing mammals or avian species with a peptide of the present invention as an antigen, and collecting blood from the mammals or avian species, and separating and purifying antibodies from the collected blood. For example, mammals such as mouse, hamster, guinea pig, chicken, rat, rabbit, dog, goat, sheep, and bovine, or avian species can be immunized. Methods of immunization are known to those skilled in the art, and the antigen can be administered, for example, two or three times at an interval of 7 to 30 days. The dosage can be, for example, approximately 0.05 mg to 2 mg of antigen per administration. The route of administration is not particularly limited, and can be suitably selected from subcutaneous administration, intradermal administration, intraperitoneal administration, intravenous administration, intramuscular administration, and such. Furthermore, the antigen can be used after dissolving it in a suitable buffer, for example, a buffer containing a conventional adjuvant such as Freund's complete adjuvant and aluminum hydroxide.

Immunized mammals or avian species can be reared for a certain period of time, and, when the antibody titer has increased, they can be additionally immunized with, for example, 100 µg to 1000 µg of the antigen. Blood can be collected from the immunized mammals or avian species one to two months after the final administration, and the blood can be separated and purified by conventional methods such as centrifugation, precipitation using ammonium sulfate or polyethylene glycol, chromatography such as gel filtration chromatography, ion exchange chromatography, affinity chromatography, and such, to obtain the polyclonal antibodies that recognize the peptides of the present invention as a polyclonal antiserum.

On the other hand, monoclonal antibodies can be obtained by preparing hybridomas. For example, hybridomas can be obtained by cell fusion of antibody-producing cells with myeloma cell lines. Hybridomas that produce monoclonal antibodies of the present invention can be obtained by cell fusion methods such as those indicated below.

Spleen cells, lymph node cells, B lymphocytes, and such from immunized animals are used as antibody-producing cells. The peptides of the present invention are used as antigens. Animals such as mouse and rat can be used as immunized animals, and administration of antigens to these animals is carried out by conventional methods. For example, animals are immunized by administering a suspension or emulsion of a peptide of the present invention, which is an antigen, with an adjuvant such as Freund's complete adjuvant and Freund's incomplete adjuvant, to the animals several times intravenously, subcutaneously, intradermally, intraperitoneally, or such. Antibody-producing cells such as spleen cells are obtained from the immunized animals, and can be fused with myeloma cells by known methods (G. Kohler et al., Nature, 256, 495 (1975)) to generate hybridomas.

For mice, examples of myeloma cell lines used for cell fusion include, for example, the P3X63Ag8, P3U1, Sp2/0 lines, etc. A fusion-promoting agent such as polyethylene glycol and Sendai virus is used for cell fusion, and hypoxanthine/aminopterin/thymidine (HAT) medium is used for selecting hybridomas by a conventional method after cell fusion. Hybridomas obtained by cell fusion are cloned by the limiting dilution method or such. As necessary, cell lines producing monoclonal antibodies that specifically recognize the peptides of the present invention can be obtained by using the peptides of the present invention in screening with an enzyme immunoassay method.

In addition to the above-mentioned methods, immunized cells can be modulated by stimulating human lymphocytes such as EB virus-infected lymphocytes in vitro using the peptides of the present invention, cells expressing the peptides, or lysates thereof. Human antibodies that bind to the peptides of the present invention can be obtained by fusing the immunized lymphocytes with human-derived bone marrow cells such as U266 (Japanese Patent Application Kokai Publication No. (JP-A) S63-17688 (unexamined, published Japanese patent application)).

In order to produce monoclonal antibodies of interest from hybridomas thus obtained, the hybridomas can be cultured by conventional culture methods or ascites-forming methods, and the monoclonal antibodies can be purified from the culture supernatant or ascites. Purification of monoclonal antibodies from culture supernatants or ascites can be performed by conventional methods. For example, ammonium sulfate fractionation, gel filtration, ion exchange chromatography, affinity chromatography, and such can be suitably combined and used.

Transgenic animals that have a group of human antibody genes can be immunized using the peptides of the present invention, cells expressing the peptides, or lysates thereof. Antibody-producing cells can be collected from the immunized transgenic animals, and fused with the above-described myeloma cell lines to obtain hybridomas. Monoclonal antibodies of interest can then be produced from the hybridomas (WO92/03918; WO94/02602; WO94/25585; WO94/33735; WO96/34096).

Furthermore, antibody-producing immune cells such as immunized lymphocytes can be immortalized using oncogenes, and used for preparation of monoclonal antibodies.

Monoclonal antibodies thus obtained can also be modulated using gene manipulation techniques (Borrbaeck and Larrick, (1990) Therapeutic Monoclonal Antibodies). For example, recombinant antibodies can be prepared by cloning a DNA encoding an antibody from antibody-producing cells such as hybridomas and immunized lymphocytes, and inserting it into a suitable vector, and introducing this into host cells.

The antibodies of the present invention may be antibody fragments or modified antibodies, as long as they bind to the peptides of the present invention. The antibody fragments can be Fab, F(ab')2, Fv, or a single chain Fv (scFv) in which Fv fragments derived from H and L chains are linked together with a suitable linker (Huston et al., (1998) Proc Natl Acad Sci USA 85: 5879-83). More specifically, the antibody fragments can be prepared by treating antibodies with an enzyme such as papain and pepsin (Co et al., (1994) J Immunol 152:2968-76; Better and Horwitz, (1989) Methods Enzymol 178: 476-96; Pluckthun and Skerra, (1989) Methods Emzymol 178:497-515; Lamoyi (1986) Methods Enzymol 121: 652-63; Rousseaux et al., (1986) Methods Enzymol 121:663-9; Bird and Walker, (1991) Trends Biotech 9:132-7).

The antibodies of the present invention include modified antibodies obtained by binding antibodies to various molecules such as polyethylene glycol (PEG). The antibodies can be modified by conventional chemical modification methods known in the art.

The antibodies of the present invention include chimeric antibodies including a variable region derived from a non-human antibody and a constant region derived from a human antibody, and humanized antibodies including a complementarity-determining region (CDR) derived from a non-human antibody, a framework region (FR) derived from a human antibody, and a constant region derived from a human antibody. Such antibodies can be prepared by conventional methods known in the art. Humanized antibodies can be obtained by substituting the CDR sequence region of a human antibody with a rodent CDR region having desired binding activity (Verhoeyen et al., (1988) Science 239:1534-6). Accordingly, compared to chimeric antibodies, humanized antibodies are antibodies in which a smaller region of a human antibody is substituted with a corresponding region of non-human origin.

A complete human antibody having a human variable region in addition to human framework and constant regions can also be produced. For example, in an in vitro method, screening can be carried out using a recombinant library of bacteriophages on which human antibody fragments are displayed (Hoogenboom and Winter, (1992) J Mol Biol 227: 381-8). Similarly, human antibodies can be produced by introducing human immunoglobulin loci into transgenic animals whose endogenous immunoglobulin genes have been partially or completely inactivated (U.S. Pat. Nos. 6,150,584, 5,545,807, 5,545,806, 5,569,825, 5,625,126, 5,633,425, and 5,661,016).

The antibodies obtained as described above can be purified to homogeneity by conventional methods in the art. For example, common methods of protein separation and purification can be used. The antibodies can be separated and purified by a combination of column chromatography such as affinity chromatography, filtration, ultrafiltration, salting out, dialysis, SDS polyacrylamide gel electrophoresis, isoelectric focusing, and such; however, separation and purification methods are not limited thereto (Antibodies: A Laboratory Manual, Ed Harlow and David Lane, (1988) Cold Spring Harbor Laboratory). Protein A columns and protein G columns can be used for affinity columns. Examples of protein A columns include HyperD, POROS, and Sepharose F.F (Pharmacia).

Examples of chromatography other than affinity chromatography include ion exchange chromatography, hydrophobic chromatography, gel filtration, reverse-phase chromatography, adsorption chromatography, and such (Strategies for Protein Purification and Characterization: A Laboratory Course Manual. Ed Daniel R. et al.). Liquid chromatography such as HPLC and FPLC can also be used for chromatography.

The antigen-binding affinity of the antibodies of the present invention may be measured using, for example, absorbance measurement, enzyme-linked immunosorbent assay (ELISA), enzyme immunoassay (EIA), radioimmunoassay (RIA), and immunofluorescence assay; however, the methods are not limited thereto. In ELISA, the antibodies of the present invention are immobilized onto a plate, and the peptides of the present invention are added, then a sample containing a culture supernatant of antibody-producing cells or purified antibodies is added. Subsequently, a secondary antibody that has a detectable label and recognizes the antibody whose antigen-binding affinity is to be measured, is added. After washing the plate, reagents for detecting the label of the secondary antibody are added and the absorbance or such is measured. For example, enzymes such as alkaline phosphatase can be used as a label for the secondary antibody, and enzyme substrates such as p-nitrophenyl phosphate can be used as a reagent for detection. BIAcore (Pharmacia) can also be used to evaluate the activity of the antibodies.

The antibodies of the present invention can detect the peptides of the present invention contained in samples. Specifically, the presence of the peptides of the present invention in cancer tissues can be confirmed, for example, by contacting cancer tissue biopsies with the antibodies of the present invention.

Prior to using the peptides of the present invention in therapy for treatment and/or prevention of cancer, it is possible to predict whether the effect is promising for a test subject before initiation of the treatment by evaluating the expression of the peptides of the present invention in the cancer to be treated using the antibodies of the present invention.

Furthermore, since the antibodies of the present invention recognize CDCA1 peptide fragments, whose expression is augmented in various cancer cells, their application is expected to be applicable not only in diagnosis but also for treatment.

(4) Helper T Cells, Killer T Cells, or Immunocyte Populations Including Them

The present invention also relates to helper T cells and killer T cells induced by in vitro stimulation using the peptides of the present invention, as well as immunocyte populations including the helper T cells and killer T cells. For example, tumor response activated T cells are induced when peripheral blood lymphocytes or tumor-infiltrating lymphocytes are stimulated in vitro using the peptides of the present invention, and these activated T cells can be effectively used for adoptive immunotherapy. Alternatively, dendritic cells which are potent antigen-presenting cells can be pulsed with the peptides of the present invention or genetically transformed to express the peptides, and anti-tumor immune response can be induced by stimulating T cells in vivo or in vitro using the dendritic cells.

Helper T cells, killer T cells, or immunocyte populations including them can be preferably induced by in vitro stimulation using the peptides of the present invention and an adjuvant. The adjuvants used herein include cell growth factors and cytokines.

Tumors can be suppressed and cancers can be prevented and/or treated by transfusion of the thus-obtained helper T cells, killer T cells, or immunocyte populations including them into a cancer patient intravascularly, locally to the tumor, or such.

Helper T cells, killer T cells, or immunocyte populations including them that are capable of suppressing tumors as described above can be produced using the peptides of the present invention. Therefore, the present invention provides cell culture media containing the peptides of the present invention. Helper T cells, killer T cells, or immunocyte populations including them capable of suppressing tumors can be prepared using the cell culture media. Furthermore, the present invention provides a cell culture kit including the above-mentioned cell culture medium and a cell culture vessel for production of helper T cells, killer T cells, or immunocyte populations including them.

(5) Antigen-Presenting Exosomes

The present invention further provides an endocytic vesicle called "exosome" which presents on its surface a complex formed between a peptide of the present invention and an HLA antigen. Exosomes can be prepared, for example, by the methods described in detail in the Japanese translations of Japanese Patent Application Kohyo Publication No. (JP-A) H11-510507 (unexamined Japanese national phase publication corresponding to a non-Japanese international publication) and JP-A (Kohyo) 2000-512161. Preferably, exosomes are prepared using antigen-presenting cells obtained from a subject of treatment and/or prevention. Exosomes of the present invention can be injected as a cancer vaccine in a similar manner as the peptides of the present invention.

The HLA antigenic type used in the present invention should match the HLA antigenic type of a subject in need of the treatment and/or prevention. For example, the HLA antigenic type is HLA-A02, and preferably, HLA-A2 (HLA-A*0201). "HLA-A2" signifies a protein while "(HLA-A*0201)" signifies a gene corresponding to a segment of the protein, because of the lack of terminology for expressing segments of the protein at present.

(6) Methods for Inducing Antigen-Presenting Cells and Killer T Cells

The present invention provides methods for inducing antigen-presenting cells using one or more of the peptides of the present invention. Antigen-presenting cells can be induced by contacting dendritic cells induced from peripheral blood monocytes with one or more of the peptides of the present invention to stimulate the dendritic cells. When the peptides of the present invention are administered into a subject, antigen-presenting cells presenting the peptides of the present invention on their surface can be induced in the body of the subject. Alternatively, an ex vivo method can be used, in which antigen-presenting cells are pulsed with the peptides of the present invention, and then the cells are administered to a subject as a vaccine. For example, ex vivo administration may include the steps of:

(1) collecting antigen-presenting cells from a subject; and
(2) contacting the antigen-presenting cells of step (1) with a peptide of the present invention (pulsing the antigen-presenting cells of step (1) with a peptide of the present invention).

The antigen-presenting cells obtained in step (2) can be administered into a subject as a vaccine.

The present invention also provides methods for inducing antigen-presenting cells that show a high level of killer T cell induction activity. The methods include the step of transfecting antigen-presenting cells in vitro with a gene including a polynucleotide encoding one or more of the peptides of the present invention. The gene to be transfected can be a DNA or RNA. For transfection, various methods conventionally performed in the art, such as lipofection, electroporation, and a calcium phosphate method can be suitably used, but the methods are not limited thereto. More specifically, transfection can be performed as described in Reeves M E, et al., (1996) Cancer Res., 56:5672-7; Butterfield L H, et al., (1998) J. Immunol., 161:5607-13; Boczkowski D, et al., (1996) J Exp. Med., 184:465-72; and WO99/08521. When the genes are transfected into antigen-presenting cells, they are transcribed and translated in the cells. The resulting proteins are subsequently processed via the MHC class I and class II pathways, and are presented on the surface of the antigen-presenting cells as partial peptides through the antigen-presenting pathway.

The present invention also provides methods for inducing killer T cells using one or more of the peptides of the present invention. By administering one or more of the peptides of the present invention to a subject, killer T cells can be induced in the body of the subject, thus augmenting the immune system that targets cancer cells presenting CDCA1 in tumor tissues. Alternatively, activated killer T cells can be induced by contacting antigen-presenting cells and CD8 positive cells from the subject with one or more of the peptides of the present invention in vitro, and by contacting peripheral-blood mononuclear leukocytes with the antigen-presenting cells in vitro to stimulate the cells. In ex vivo therapeutic methods, the immune system that targets cancer cells presenting CDCA1 in tumor tissues in a subject can be augmented by returning the activated killer T cells into the body of the subject. For example, the methods include the steps of (1) collecting antigen-presenting cells from a subject;
(2) contacting the antigen-presenting cells of step (1) with a peptide of the present invention (pulsing the antigen-presenting cells of step (1) with a peptide of the present invention);
(3) mixing and co-culturing the antigen-presenting cells of step (2) with $CD8^+$ T cells to induce cytotoxic T cells; and
(4) collecting $CD8^+$ T cells from the co-culture of step (3).

$CD8^+$ T cells having cytotoxic activity obtained in step (4) can be administered to a subject as a vaccine.

The present invention also provides isolated killer T cells induced using one or more of the peptides of the present invention. Preferably, killer T cells induced by the method of the present invention are derived from a subject who receives the treatment and/or prevention. The cells can be administered in combination with other agents containing antigen-presenting cells or exosomes presenting one or more of the peptides of the present invention. The obtained killer T cells are specific to target cells presenting the same peptide used for induction. The target cells are cells endogenously expressing CDCA1, or cells transfected with the CDCA1 gene. By stimulation with a peptide of the present invention, cells presenting the peptide of the present invention on their surface, such as cancer cells from lung cancer, cholangiocellular carcinoma, bladder cancer, renal cell carcinoma, prostate cancer, chronic myelogenous leukemia, malignant lymphoma, cervical cancer, osteosarcoma, breast cancer, soft tissue sarcoma, colon cancer, and such, can become targets for attack.

(7) T Cell Receptors (TCR)

The present invention further provides nucleic acids encoding the polypeptides forming the subunits of T cell receptors (TCRs) that recognize CDCA1-1 and CDCA1-4, and methods for their use. TCR contains at least seven transmembrane proteins. A disulfide bond-linked ($\alpha$, $\beta$) heterodimer forms the clonotypic antigen recognition unit, while the invariant CD3 chains which consist of $\epsilon$, $\gamma$, $\delta$ and $\zeta$, and $\eta$ chains couple the ligand binding with the signaling pathway, thereby causing T cell activation and cellular immune response. The $\alpha$ and $\beta$ subunits, which are responsible for antigen recognition as mentioned above, are necessary for T cells to acquire the specificity of recognition for a particular target. Therefore, to synthesize TCRs that specifically recognize the peptides of the present invention, the nucleic acid sequences of α and β which are TCR subunits derived from CTLs induced using the peptides of the present invention can be identified by methods known to those skilled in the art (WO2007/032255; and Morgan et al., J. Immunol., 171, 3288 (2003)). Since TCRs formed from the identified TCR subunits can bind to CDCA1 peptide-presenting target cells, the TCRs are useful when introduced into cells having cell-killing effect.

Nucleic acids encoding the TCR subunits can be incorporated into suitable vectors (for example, retroviral vectors). The vectors can be produced by methods known to those skilled in the art. The TCR subunit-incorporated vectors can be used for introduction into T cells. In particular, by transforming patient-derived T cells, T cells (CTLs) that specifically recognize and attack CDCA1 expressing cells can be obtained. TCR-introduced CTLs thus obtained can be cultured and grown by common methods (Kawakami et al., J. Immunol., 142, 3452-3461 (1989)). CTLs obtained by the above-mentioned method can be used for cellular immunotherapy.

The present invention also provides antigen-presenting cells presenting a complex formed with an HLA antigen and one or more of the peptides of the present invention. The antigen-presenting cells, with which one or more of the peptides of the present invention or nucleotides encoding such peptides are contacted, are preferably collected from a subject who receives the treatment and/or prevention. The peptides of the present invention, antigen-presenting cells presenting the peptides, exosomes, or activated killer T cells can be administered as a vaccine in combination with other drugs.

All prior art references cited in the present specification are incorporated herein by reference.

The present invention will be further described with reference to the Examples below; however, it is not to be construed as being limited thereto.

EXAMPLES

Example 1

(1) Selection of a CDCA1 Peptide Repertoire that Shows Affinity to HLA-A2

The amino acid sequence of human CDCA1 was searched using the BIMAS system, and 41 types of peptides were selected in the descending order of estimated binding affinity to HLA-A2 (Table 1).

TABLE 1

| No. | PEPTIDE POSITION | PEPTIDE AMINO ACID SEQUENCE | BINDING AFFINITY SCORE | SEQUENCE ID NUMBER |
|---|---|---|---|---|
| 1 | 65-73 | YMMPVNSEV | 855 | SEQ ID NO: 1 |
| 2 | 120-128 | FLSGIINFI | 607 | SEQ ID NO: 3 |
| 3 | 222-230 | RLNELKLLV | 285 | SEQ ID NO: 4 |
| 4 | 351-359 | KLATAQFKI | 211 | SEQ ID NO: 2 |
| 5 | 182-190 | QLSDGIQEL | 201 | SEQ ID NO: 5 |
| 6 | 141-149 | FLWQYKSSA | 190 | SEQ ID NO: 6 |
| 7 | 3-11 | TLSFPRYNV | 69.6 | SEQ ID NO: 7 |
| 8 | 285-293 | CLPSCQLEV | 69.6 | SEQ ID NO: 8 |
| 9 | 386-394 | AVYERVTTI | 27.5 | SEQ ID NO: 9 |
| 10 | 372-380 | TVIEDCNKV | 25.0 | SEQ ID NO: 10 |
| 11 | 243-251 | KIVDSPEKL | 20.7 | SEQ ID NO: 11 |
| 12 | 257-265 | KMKDTVQKL | 17.8 | SEQ ID NO: 12 |
| 13 | 88-96 | LVTHLDSFL | 17.5 | SEQ ID NO: 13 |
| 14 | 447-455 | KIDEKTAEL | 16.9 | SEQ ID NO: 14 |
| 15 | 358-366 | KINKKHEDV | 16.4 | SEQ ID NO: 15 |
| 16 | 416-424 | KLKSQEIFL | 14.4 | SEQ ID NO: 16 |
| 17 | 82-90 | FLPFSNLVT | 14.1 | SEQ ID NO: 17 |
| 18 | 344-352 | LMIVKKEKL | 12.9 | SEQ ID NO: 18 |
| 19 | 109-117 | ILCPKAKRT | 12.9 | SEQ ID NO: 19 |
| 20 | 44-52 | VLHMIYMRA | 12.7 | SEQ ID NO: 20 |
| 21 | 228-236 | LLVVSLKEI | 40.8 | SEQ ID NO: 21 |
| 22 | 227-236 | KLLVVSLKEI | 311 | SEQ ID NO: 22 |
| 23 | 222-231 | RLNELKLLVV | 269 | SEQ ID NO: 23 |

TABLE 1-continued

| No. | PEPTIDE POSITION | PEPTIDE AMINO ACID SEQUENCE | BINDING AFFINITY SCORE | SEQUENCE ID NUMBER |
|---|---|---|---|---|
| 24 | 294-303 | QLYQKKIQDL | 157 | SEQ ID NO: 24 |
| 25 | 87-96 | NLVTHLDSFL | 117 | SEQ ID NO: 25 |
| 26 | 181-190 | KQLSDGIQEL | 64.5 | SEQ ID NO: 26 |
| 27 | 47-56 | MIYMRALQIV | 49.1 | SEQ ID NO: 27 |
| 28 | 402-411 | KLGIQQLKDA | 40.0 | SEQ ID NO: 28 |
| 29 | 343-352 | RLMIVKKEKL | 38.7 | SEQ ID NO: 29 |
| 30 | 309-318 | KLASILKESL | 36.6 | SEQ ID NO: 30 |
| 31 | 22-31 | ILTGADGKNL | 36.3 | SEQ ID NO: 31 |
| 32 | 193-202 | SLNQDFHQKT | 28.3 | SEQ ID NO: 32 |
| 33 | 52-61 | ALQIVYGIRL | 21.4 | SEQ ID NO: 33 |
| 34 | 44-53 | VLHMIYMRAL | 16.7 | SEQ ID NO: 34 |
| 35 | 35-44 | DLYPNPKPEV | 16.7 | SEQ ID NO: 35 |
| 36 | 165-174 | KLERLDSVPV | 15.6 | SEQ ID NO: 36 |
| 37 | 65-74 | YMMPVNSEVM | 12.3 | SEQ ID NO: 37 |
| 38 | 154-163 | QLNAAHQEAL | 10.5 | SEQ ID NO: 38 |
| 39 | 60-69 | RLEHFYMMPV | 10.2 | SEQ ID NO: 39 |
| 40 | 344-353 | LMIVKKEKLA | 6.1 | SEQ ID NO: 40 |
| 41 | 453-462 | AELKRKMFKM | 4.8 | SEQ ID NO: 41 |

The HLA-A2 restricted killer T cell epitopes identified in the present invention are underlined.

Example 2

First, dendritic cells (DCs) were induced from bone marrow cells of HLA-A2 transgenic mice using a previously reported method (Komori H et al. Clinical Cancer Research 12: 2689-2697, 2006). BM-DCs thus obtained were pulsed with a CDCA1 peptide (10 µM), and then administered intraperitoneally to HLA-A2 transgenic mice at $5\times10^5$ cells per mouse. The mice were immunized twice at one week interval by the same administration method, then their spleen cells were collected and used for detection of killer T cells. In order to rigorously examine the induction of killer T cells derived from CD8$^+$ T cells, CD4$^+$ T cells were eliminated from the spleen cells using MACS beads after removal of the spleen, and the remaining cells were used.

FIG. 1A shows the protocol for determining the CDCA1 peptides recognized by HLA-A2 restricted killer T cells in HLA-A2 transgenic mice. The day when spleen cells were collected from the immunized mice is designated as "Day 0".

Day −21: (1) Induction of bone marrow-derived dendritic cells (herein below, referred to as BM-DCs) was initiated by adding GM-CSF to the bone marrow cells of HLA-A2 transgenic mice.

Day −14: (2) A mixture of four types of CDCA1 peptides was added to the induced BM-DCs, and after two hours, this was administered intraperitoneally at $5\times10^5$ cells per mouse.

(1) and (2) were repeated twice at one week interval.

Day 0: Spleen cells were collected from the immunized HLA-A2 transgenic mice, and co-cultured with BM-DCs that had been incubated with CDCA1 peptides for two hours. This was subsequently cultured for six days.

Day 6: To detect killer T cells that specifically recognize CDCA1 peptides, T cells that produce gamma interferon after antigenic stimulation were quantified by ELISPOT assay. As target cells, BM-DCs pulsed with each individual CDCA1 peptide and unpulsed BM-DCs were used.

Figure 2:
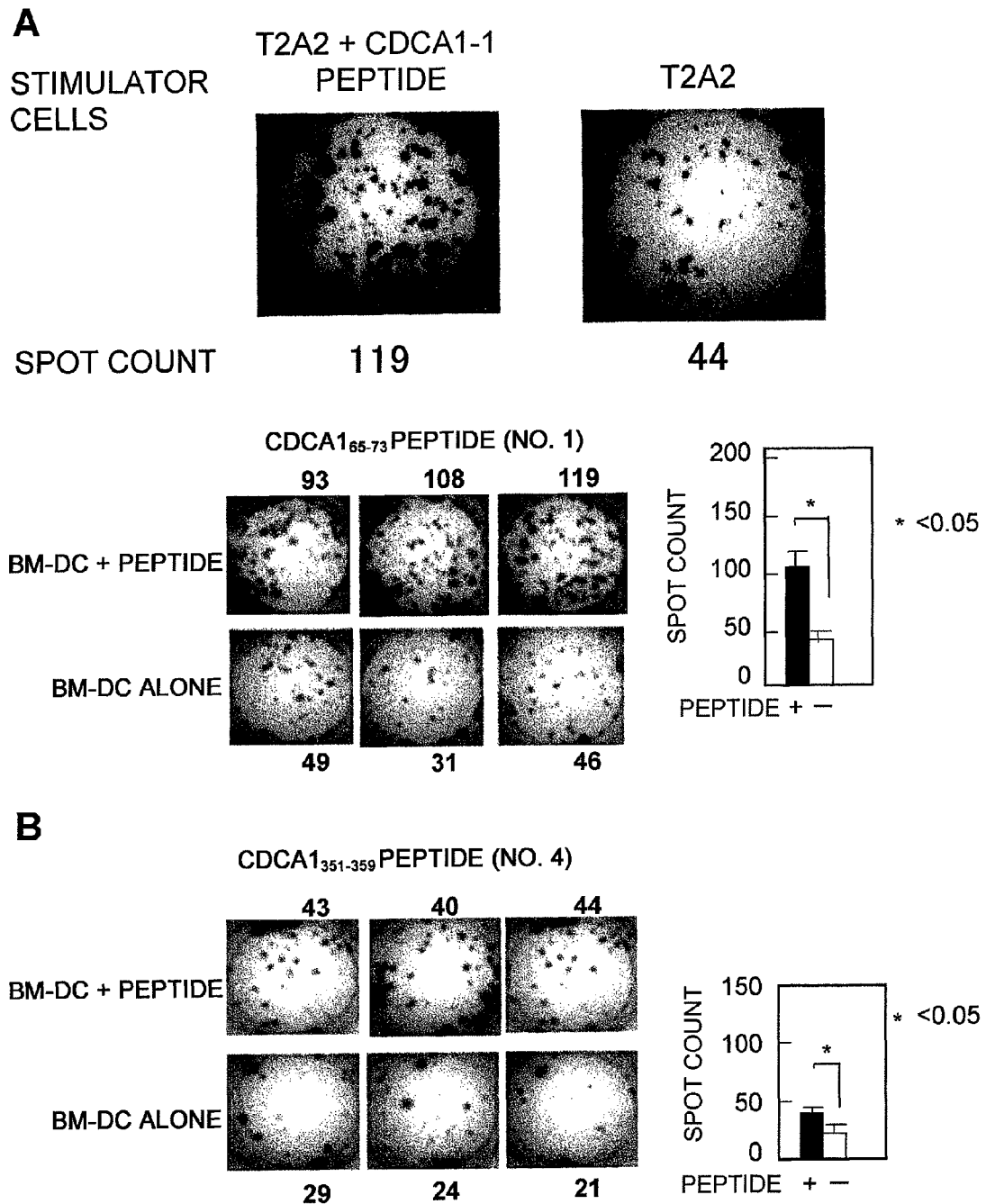
FIG. 2 shows the result of ELISPOT assay for detecting IFN-γ produced by killer T cells activated as a result of specific recognition of CDCA1 peptides.

Evaluation of the Activity of CDCA1 Specific Killer T Cells by ELISPOT Assay:

It was determined by ELISPOT assay whether or not killer T cells that specifically react with CDCA1 to produce IFN-γ actually exist among the induced killer T cells. IFN-γ was detected using a Mouse IFN-γ ELISPOT Set (BD Biosciences). When killer T cells (effectors) respond to stimulator cells (targets) and produce IFN-γ, they are detected as red spots. As target cells, HLA-A2 positive T2A2 cells that do not express CDCA1 and CDCA1 peptide-pulsed T2A2 cells were used. T2A2 cells, a cell line produced by introducing the HLA-A2 gene into the mouse T2 cell line deficient in the TAP gene expression, were purchased from RIKEN Cell Bank. Due to the TAP deficiency in these cells, complexes formed between HLA-A2 molecules and exogenously added peptides are expressed on the cell surface only when the peptides have the capacity of binding to the HLA-A2 molecules. First, ELISPOT plates (BD Biosciences) were coated with an anti-mouse IFN-γ antibody for 18 hours. Subsequently, the plates were blocked with 10% FCS/RPMI for two hours. Effector cells (100 µL/well) and target cells (100 µL/well) were mixed and cultured for 22 hours at 37° C. The experiment was conducted at an effector/target ratio (E/T ratio) of 5:1. The plates were then washed with sterilized water, and reacted with a biotinylated anti-mouse IFN-γ antibody for two hours, and further reacted with streptavidin-HRP for one hour. IFN-γ positive spots were detected using a substrate solution. An automatic analysis software of MINERVA TECH was used to count the spots. The results for Peptide Numbers 1 to 20 are shown in FIG. 1B. From similar experiments, CDCA1 specific killer T cell immune response was observed in killer T cells induced with the CDCA1$_{65-73}$ (No. 1) (SEQ ID NO: 1) or CDCA1$_{351-359}$ (No. 4) (SEQ ID NO: 2) peptide among the 41 peptides (FIG. 2).

The analysis results of killer T cells induced with the CDCA1$_{65-73}$ (No. 1) (SEQ ID NO: 1) or CDCA1$_{351-359}$ (No. 4) (SEQ ID NO: 2) peptide are shown in FIGS. 2A and 2B, respectively.

Example 3

Patients, Blood Samples, and Cell Lines:

Blood samples derived from NSCLC patients were collected during routine diagnostic examinations with informed consent. The CDCA1 negative human colon cancer cell line COLO201 was provided by the Health Science Research Resources Bank. The HLA-A2 expression in these samples was confirmed by flow cytometry using the HLA-A2 monoclonal antibody BB7.2 (One Lambda Inc., Canoga Park, Calif.).

Lentiviral Gene Transfer:

Lentiviral vector-mediated gene transfer was performed using the method described in Tahara-Hanaoka S, et al. Exp. Hematol. 2002; 30:11-17. Briefly, 17 μg of CDCA1 cDNA-carrying CSII-CMV-RfA and CSIIEF-RfA self-inactivating vectors (Miyoshi H, et al. J. Virol. 1998; 72:8150-8157) and 10 μg of pCMV-VSV-G-RSV-Rev and pHIVgp were transfected into 293T cells on a 10 cm culture dish using Lipofectamine 2000 (Invitrogen Corporation, Carlsbad, Calif., USA). After 60 hours, the culture medium was collected and viral particles were pelleted by ultracentrifugation (50,000× g, two hours). The pellet was suspended in 50 μL of RPMI 1640 solution, and 10 μL of the viral suspension was added to each well of a U-bottomed 96-well plate containing 5×10$^4$ COLO201 cells per well. Expression of the transfected CDCA1 gene was confirmed by Western blot analysis.

Induction of CDCA1 Reactive Human CTLs:

Monocyte-derived DC cells were used as antigen-presenting cells for induction of CTLs in response to HLA-presented peptides. DCs were obtained by previously reported in vitro methods (Suda T, et al. Cancer Sci. 2007; Nakahara S, et al. Cancer Res. 2003; 63:4112-8). Briefly, peripheral blood monocytes (PBMCs) isolated from HLA-A*0201 positive healthy volunteers and NSCLC patients using a Ficoll-Paque solution (GE Healthcare UK, Ltd., Buckinghamshire, UK) were screened for CD8 positive CD14 positive populations using MicroBeads (Miltenyi Biotec, Bergisch Gladbach, Germany). To obtain DCs, the CD14 positive population was cultured in AIM-V (Invitrogen) containing 2% autologous plasma in the presence of 100 ng/mL of granulocyte-macrophage colony stimulating factor (GM-CSF) and 10 ng/mL of interleukin (IL)-4 (PeproTec Inc., New Jersey, USA). Four days after incubation, OK-432 was added to the dish to prepare mature DCs. Five days after the start of culture for cytokine-induced DCs, the cells were pulsed with 20 μg/mL of an HLA-A2 binding peptide for two hours at 37° C. in AMI-V in the presence of 4 μg/mL off β2-microglobulin (Sigma-Aldrich, St. Louis, Mo., USA). These peptide-pulsed DCs were irradiated (3,500 cGy) and mixed at a 1:50 ratio with autologous CD8 positive T cells obtained from PBMCs using anti-CD8 MicroBeads (Miltenyi Biotec). The incubation was carried out using 48-well plates, which were prepared to contain 0.5 mL of AIM-V containing in each well 2% autologous plasma, 1×10$^4$ peptide-pulsed DCs, 5×10$^5$ CD8 positive T cells, and 10 ng/mL of human IL-7 (Wako, Osaka, Japan). Three days after incubation, human IL-2 (PeproTec Inc.) was added at a concentration of 20 IU/mL. Furthermore, the T cells were restimulated with peptide-pulsed autologous DCs on days 12 and 19. DCs were suitably prepared by the above-mentioned method. Six days after the third peptide stimulation on day 25, the antigen-specific CTL response was evaluated by Chromium (Cr) release assay and IFN-γ ELISPOT assay.

CTL Response to Target Cells:

CTLs were co-cultured at various effector cell/target cell ratios with target cells which are various cancer cell lines and T2 cells with or without peptide pulsing, and $^{51}$Cr release assay and IFN-γ ELISPOT assay were conducted using conventional methods (Komori H, et al., Clin. Cancer Res. 2006; 12:2689-2697; Makita M, et al. Clin. Cancer Res. 2002; 8:2626-31; Yokomine K, et al. Cancer Sci. 2007; 98:1930-5). Briefly, target cells were labeled using 3.7 KBq Na$_2$ $^{51}$Cr$_4$ (Perkin Elmer Life Sciences) at 37° C. for one hour in a CO$_2$ incubator. The labeled target cells were rinsed three times, and peptide-pulsed target cells were prepared by incubating the cells with 20 μg/mL of a peptide for three hours at 37° C. The target cells were mixed with effector cells to a final volume of 200 μL on a flat-bottomed microtiter plate, and then incubated. Six hours after incubation, 50 μL of the supernatant was collected from each well, and radioactivity was quantified using a gamma counter. The specific cytotoxic activity was evaluated by calculating the specific $^{51}$Cr release rate according to an existing method (Suda T, et al. Cancer Sci. 2007; 98:1803-8). ELISPOT assay was also performed according to an existing method (Komori H, et al. Clin. Cancer Res. 2006; 12:2689-97).

Figure 3:
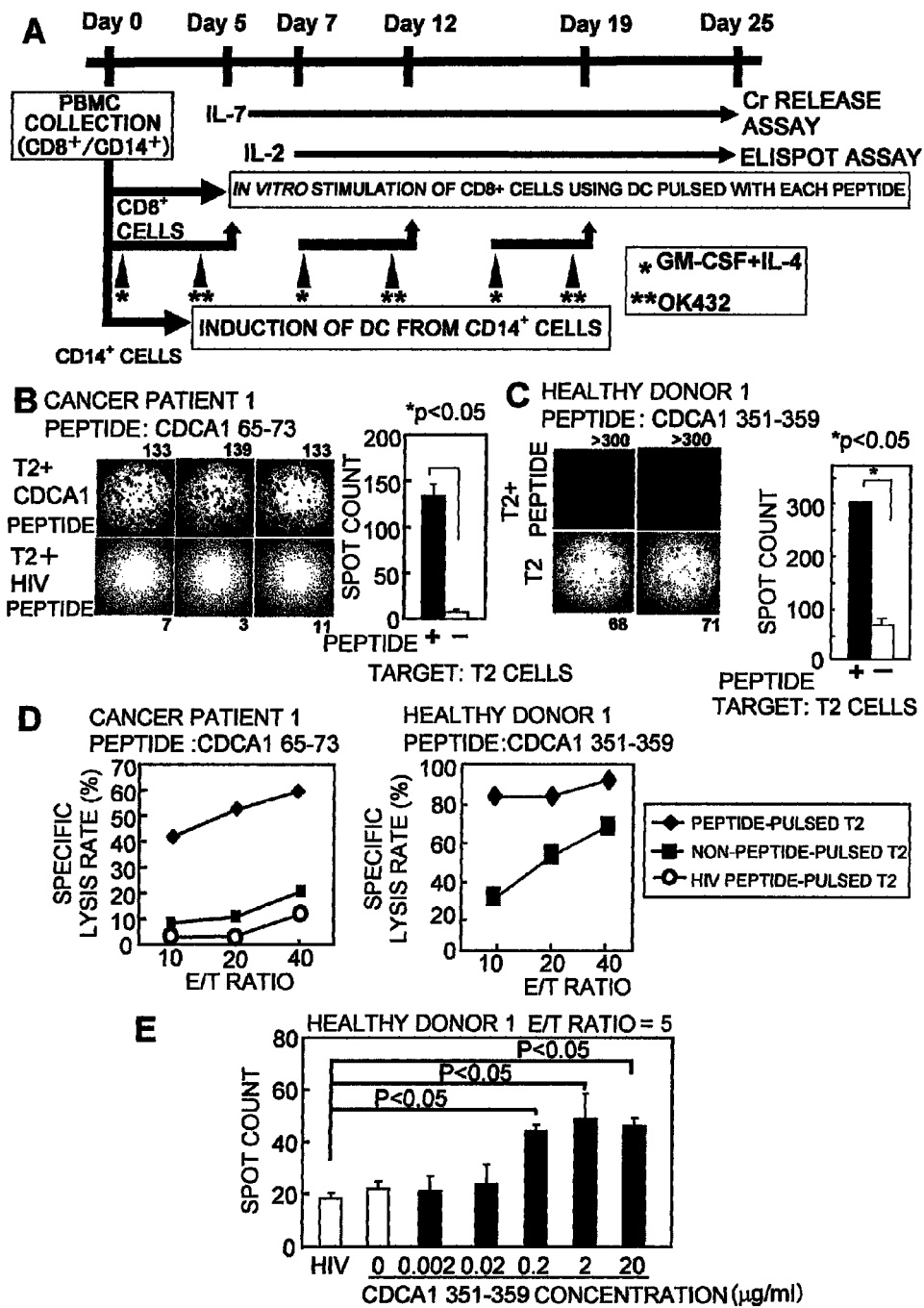
FIG. 3 shows CDCA1 specific immune response of CTLs induced from a healthy donor.

Induction of CDCA1 Responsive CTLs from PBMCs Derived from HLA-A2 Positive Healthy Donors:

PBMCs were isolated from HLA-A2 (A*0201) positive healthy donors. CD8$^+$ T cells were co-cultured with monocyte-derived DCs pulsed with the CDCA1$_{65-73}$ (No. 1) (SEQ ID NO: 1) or CDCA1$_{351-359}$ (No. 4) (SEQ ID NO: 2) peptide, and the CD8$^+$ T cells were stimulated three times a week (FIG. 3A).

CTLs induced from cancer patients or healthy donors were co-cultured with target cells. T2 cells pulsed with the CDCA1$_{65-73}$ (No. 1) (SEQ ID NO: 1) or CDCA1$_{351-359}$ (No. 4(SEQ ID NO: 2) peptide were used as the target, and ELISPOT assay and $^{51}$Cr release assay were performed. As shown in FIG. 3B, for cancer patient donor 1, the IFN-γ production by CTLs was significantly greater when the cells were stimulated with CDCA1$_{65-73}$ (No. 1) (SEQ ID NO: 1) peptide-pulsed T2 than with unpulsed T2. CTLs induced from healthy donor 1 produced a large amount of IFN-γ in response to CDCA1$_{351-359}$ (No. 4) (SEQ ID NO: 2) peptide-pulsed T2 cells (more than 300 spots per well) (FIG. 3C). Furthermore, CTLs derived from cancer patient donor 1 and healthy donor 1 showed cytotoxic activity against T2 cells pulsed with the CDCA1$_{65-73}$ (No. 1) (SEQ ID NO: 1) or CDCA1$_{351-359}$ (No. 4) (SEQ ID NO: 2) peptide in release assay (FIG. 3D). As shown in FIG. 3E, when CTLs were stimulated by T2 cells pulsed with the CDCA1 peptide at various concentrations, the CTLs responded to the CDCA1 peptide-pulsed T2 cells in a dose-dependent manner. Compared to the response to unpulsed T2 cells or to T2 cells pulsed with an HLA-A2 binding HIV-derived peptide, CTLs were found to produce a larger amount of IFN-γ in response to T2 cells pulsed at a peptide concentration of 0.2 μg/mL or more.

The above-mentioned results show that these CTLs have peptide-specific cytotoxicity.

COLO201 into which CDCA1 was introduced (COLO201/CDCA1, CDCA1+, HLA-A2+; FIG. 4A) was used as target cells to examine the CDCA1 specific immune response of CTLs. As shown in FIG. 4B, healthy donor-derived CTLs stimulated with the CDCA1$_{65-73}$ (No. 1) (SEQ ID NO: 1) peptide produced a larger amount of IFN-γ against COLO201/CDCA1 than to empty vector-transfected COLO201 that does not express CDCA1. Healthy donor 2-derived CTLs stimulated with the CDCA1$_{351-359}$ (No. 4) (SEQ ID NO: 2) peptide also showed specific immune response to COLO201/CDCA1 (FIG. 4C). Furthermore, these CTLs showed immune response to PANC1 cells (CDCA1+, HLA-A2+), but not to A549 cells (CDCA1+, HLA-2−) (FIG. 4D).

To apply CDCA1 derived peptides to cancer immunotherapy, it would be most important for the CDCA1 peptide-responsive CTLs to be able to show specific cytotoxicity against tumor cells that endogenously express CDCA1. As shown in FIG. 4E, for cancer patient donor 1, CDCA1 reactive CTLs obtained using the CDCA1$_{65-73}$ (No. 1) (SEQ ID NO: 1) peptide showed cytotoxic activity against PANC1 cells (CDCA1+, HLA-A2+), but not to A549 cells (CDCA1+, HLA-2−) or COLO201 cells (CDCA1−, HLA-A2+). Similarly, healthy donor 1-derived CTLs stimulated with the CDCA1$_{351-359}$ (No. 4) (SEQ ID NO: 2) peptide showed cytotoxic activity to PANC1 cells (CDCA1+, HLA-A2+), but not to A549 cells (CDCA1+, HLA-2−). These results show that these peptides are naturally processed in cancer cells and presented on the surface of cancer cells together with HLA-A2, and can be recognized by CTLs. For detection of HLA-A2 restricted CDCA1 specific CTLs, the CDCA1$_{351-359}$ peptide-bound PE-labeled HLA-A*0201 tetramer was purchased from Medical & Biological Laboratories Co. Ltd. (Nagoya, Japan). As shown in FIG. 4G, among CD8 positive cells, a strong correlation was observed between the CDCA1$_{351-359}$ peptide-reactive CTLs and the tetramer positive CTLs. This result proves that HLA-A2 restricted CDCA1 peptide-specific CTLs were present among the CD8 positive T cells used in this study.

Discussion:

Identification of TAA-derived peptides that are naturally processed and presented on tumor cells is important for the establishment of peptide-based cancer immunotherapy. CDCA1 which is a novel cancer/testis antigen was identified by cDNA microarray analysis using NSCLC and normal tissues. CDCA1 is strongly expressed in NSCLC and normal testis, but its mRNA or protein was not expressed in the other normal tissues examined. Since the testis is a tissue isolated from the immune system, CDCA1 responsive CTLs would attack only NSCLC. Therefore, CDCA1 was selected as a TAA for immunotherapy of NSCLC patients.

To minimize the risk of deletion, mutation, or decreased expression of TAA as means for immune evasion by cancer cells as a result of immune induction therapy, it was desired to identify TAAs essential for the proliferation or survival of NSCLC that can be used as targets for immunotherapy (Yoshitake Y, et al. Clin. Cancer Res. 2004; 10:6437-48). It has been reported that CDCA1 functions to act on the attachment between spindle microtubules and kinetochores, and has an important role in the maintenance of cell cycle (De-Luca J C, et al. J. Cell Biol. 2002; 159:549-55). Furthermore, CDCA1 is a component of the nuclear division cycle (NDC) complex, which plays an important role in the appropriate chromosomal segregation during mitosis, and is highly conserved regardless of species (DeLuca J C, et al. Curr. Biol. 2003; 13:2103-9). CDCA1 is essential for the kinetochore localization of centromere protein E (CENP-E) in HeLa cells. The suppression of CDCA1 expression by siRNA causes abnormal chromosomal segregation by mitosis block and subsequent induction of cell death (Liu D, et al. J. Biol. Chem. 2007; 282:21415-24). This aberrant exit from mitosis has the characteristics of both apoptosis and catastrophe (DeLuca J C; et al. J. Cell Biol. 2002; 159:549-55). That is, CDCA1 is essential for cellular function and plays an important role in the proliferation and survival of cancer cells.

CDCA1 and kinetochore associated 2 (KNTC2) are members of the evolutionarily conserved centromere protein complex (Hayama S, et al. Cancer Res 2006; 66:10339-48). Immunostaining shows that their elevated expression is associated with a poor prognosis of NSCLC patients (Hayama S, et al. Cancer Res 2006; 66:10339-48). Therefore, the expression level of CDCA1 in NSCLC tissues is a useful marker for predicting the prognosis of patients after surgical operation. The involvement of CDCA1 in the progression of NSCLC is suggested. Thus, immunotherapy that targets CDCA1 may be effective for NSCLC patients with a poor prognosis.

Figure 4:
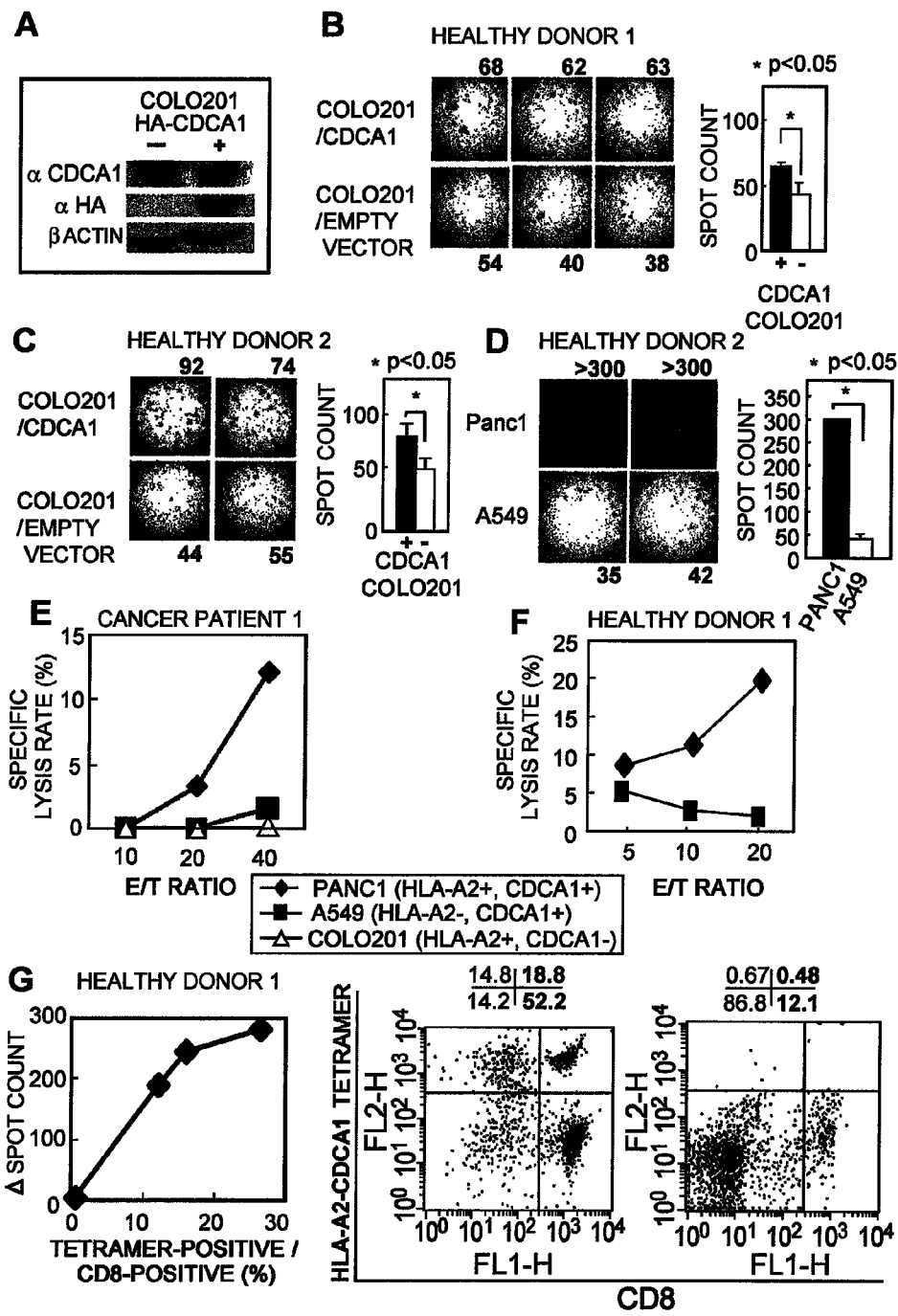
FIG. 4 shows the specific cytotoxic activity of CTLs induced from a healthy donor against CDCA1 positive cancer cells.

In the present invention, two HLA-A2 restricted CDCA1 epitope peptides that promoted the production of HLA-A2 restricted mouse CTLs were identified using HLA-A2 transgenic mice. In addition, CDCA1 reactive human CTLs could be prepared from healthy donor-derived PBMCs stimulated with these peptides. These CDCA1 peptide-specific CTL lines killed cancer cells that express CDCA1 in an HLA-A2 restricted manner (FIG. 4).

CDCA1 derived peptides predicted to have high binding affinity to the HLA-A0201 molecule were selected using the BIMAS software; however, some of the amino acid sequences are not conserved between human and mouse CDCA1. There are two amino-acid differences between the human and mouse sequences of the CDCA1$_{65-73}$ (No. 1) peptide (human: YMMPVNSEV/mouse: YMMPMNIEV), and one amino-acid difference in the CDCA1$_{351-359}$ (No. 4) peptide (human KLATAQFKI/mouse KLATARFKI). However, in the present invention, induction of the above-mentioned epitope peptide-reactive CTLs from healthy donors was confirmed.

CDCA1 reactive CTLs were induced from healthy donor-derived PBMCs by in vitro stimulation using the CDCA1 peptides. CTLs induced by peptide-presenting DCs showed cytotoxic activity against CDCA-expressing cancer cells in an HLA-A2 restricted manner. Induction of healthy donor-derived CDCA1 specific CTLs is meaningful for the continuation of further search for TAAs. Furthermore, induction of CDCA1 reactive CTLs from PBMCs isolated from patients with NSCLC, small-cell cancer, cholangiocellular carcinoma, bladder cancer, and renal cell cancer is currently being attempted. There are several cell-mediated cancer immunotherapy methods including peptide or protein vaccination (Rosenberg S A, et al. Nat Med 1998; 4:321-7), immunization with dendritic cells pulsed with peptides, proteins, or tumor lysates (Kugler A, et al. Nat Med 2000; 6:332-6), and ex vivo adoptive transfer using tumor-specific CTL lines (Falkenburg J H, et al. Blood 1999; 94:1201-8). The CDCA1 peptides identified in the present invention could be applied to these immunotherapies.

If the safety and effectiveness of cancer immunotherapy using peptides identified in the present invention, which are presented to killer T cells via HLA-A2, can be shown in investigative medicine, clinical application to Caucasians would be possible. Furthermore, by identifying peptides presented to killer T cells via HLA-A2 which is frequently possessed not only by the Japanese but also by Caucasians, it would be highly possible to develop cancer immunotherapy agents that are applicable to 30% of the Japanese and Caucasian lung cancer patients.

INDUSTRIAL APPLICABILITY

HLA-A2 is an HLA class I allele possessed by approximately 30% of the Japanese population. The CDCA1 peptides according to the present invention can induce human cytotoxic T cells that damage cancer cells expressing complexes of the peptides and HLA-A2 molecules. Therefore, the peptides according to the present invention can be applied to immunotherapies of lung cancer, cholangiocellular carcinoma, bladder cancer, renal cell carcinoma, prostate cancer, chronic myelogenous leukemia, malignant lymphoma, cervical cancer, osteosarcoma, breast cancer, soft tissue sarcoma, and colon cancer, in HLA-A2 positive patients. Thus, the peptides are useful for the development of therapeutic agents for suppressing the proliferation and progression of these cancers.

The invention claimed is:

1. An isolated peptide of (A) or (B) below:
   (A) a peptide of less than 15 amino acids comprising the amino acid sequence of SEQ ID NO: 2;
   (B) a peptide of less than 15 amino acids which comprises the amino acid sequence of SEQ ID NO: 2, in which one or two amino acid(s) are substituted, deleted, inserted, and/or added, and wherein the peptide shows cytotoxic (killer) T cell-inducing activity.

2. The peptide of claim 1, wherein the second amino acid from the N terminus of the amino acid sequence of SEQ ID NO:2 is substituted with methionine.

3. The peptide of claim 1, wherein the C-terminal amino acid of the amino acid sequence of SEQ ID NO:2 is substituted with valine or leucine.

4. An agent for inducing cytotoxicity against cancer cell expressing CDCA1, which comprises one or more peptide(s) of claim 1 as an active ingredient.

5. An agent comprising one or more peptide(s) of claim 1 as an active ingredient.

6. An agent for inducing an antigen-presenting cell that shows cytotoxic (killer) T cell-inducing activity, wherein said agent comprises one or more peptide(s) of claim 1 as an active ingredient.

7. An agent for inducing a cytotoxic (killer) T cell, wherein said agent comprises one or more peptide(s) of claim 1 as an active ingredient.

8. A method for inducing an antigen-presenting cell that shows cytotoxic (killer) T cell-inducing activity, which comprises the step of contacting an antigen-presenting cell with the peptide of claim 1.

9. A method for inducing a cytotoxic (killer) T cell, which comprises the step of contacting a T cell with the peptide of claim 1.

10. A method for inducing cytotoxicity against cancer, which comprises the step of administering the peptide of claim 1 to a subject.

11. A method of inducing a cytotoxic (killer) T cell, which comprises the step of:
   (a) contacting an antigen-presenting cell with the peptide of claim 1; and
   (b) mixing and co-culturing the antigen-presenting cell of step (a) with a $CD8^+$ T cell.

* * * * *